US006465644B1

(12) United States Patent
Yan et al.

(10) Patent No.: US 6,465,644 B1
(45) Date of Patent: Oct. 15, 2002

(54) SULFONATED [8,9] BENZOPHENOXAZINE DYES AND THE USE OF THEIR LABELLED CONJUGATES

(75) Inventors: Xiongwei Yan, Dublin; Pau Miau Yuan, San Jose, both of CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/564,417

(22) Filed: May 2, 2000

(51) Int. Cl.$^7$ .............................................. C07D 265/34
(52) U.S. Cl. .................. 544/99; 530/391.3; 530/391.5; 530/402; 530/409; 536/23.1; 536/25.32
(58) Field of Search .......................... 544/99; 530/409, 530/391.3, 391.5, 402; 536/29.32, 23.1

(56) References Cited

U.S. PATENT DOCUMENTS

| | | | |
|---|---|---|---|
| 3,655,601 A | 4/1972 | Ottawa et al. | 260/242 |
| 4,237,281 A | 12/1980 | Long | 544/99 |
| 4,714,763 A | 12/1987 | Thodoropulos | 544/31 |
| 4,962,197 A | 10/1990 | Foley et al. | 544/31 |
| 5,366,860 A | 11/1994 | Bergot et al. | 435/6 |
| 5,770,716 A | 6/1998 | Khan et al. | 536/23.1 |
| 5,792,389 A | 8/1998 | Hammond et al. | 252/582 |
| 5,936,087 A | 8/1999 | Benson et al. | 546/33 |

FOREIGN PATENT DOCUMENTS

| | | |
|---|---|---|
| EP | 0019198 A | 11/1980 |
| WO | WO97/29154 | 8/1997 |
| WO | WO99/15517 | 4/1999 |

OTHER PUBLICATIONS

Fischer et al., Chemical Abstracts, vol. 94:66426, 1981.*
Stuka et al., Chemical Abstracts, vol. 70:43661, 1969.*
Becker et al., "The Photosensitizers Benzophenoxazine and Thiazines: Comprehensive Investigation of Photophysical and Photochemical Properties," *Photochemistry and Photobiology* 51(5):533–538 (1990).

Briggs et al., "Synthesis of Functionalised Fluorescent Dyes and Their Coupling to Amines and Amino Acids," *J. Chem. Soc.*, Perkin–Trans. 1:1051–1058 (1997).

Cincotta et al., "Novel Red Absorbing Benzo[a]phenoxazinium and Beno[a]phenothiainium Photosensitizers: in vitro Evaluation," *Photochemistry and Photobiology* 46(5) 751–758 (1987).

VanAllan et al., "The Reaction of 12H–Benzo[a]phenothiazine and 12H–Benzo[b]phenoxazine with Certain Heterocyclic Azides," *J. Org. Chem.* 34 (6):1691–1694 (1969).

V. Stuzka et. al.: "Infrared Spectroscopy of Benzo(a)phenoxazines" Spectrochim. Acta, Part A (1967), vol. 23, No. 7, 1967, pp. 2175–2183.

V. Stuzka et al.: "Oxazines as Acid–Base Indicators ; Some Meldola's Blue" Chemicke Zvesti (1968), vol. 22, No. 6, 1968, pp. 431–438.

Okafor C.O.: "Synthesis, Properties and Use of Angular Phenoxazines" Dyes and Pigments, Elsevier Applied Science Publishers. Barking, GB, vol. 7, No. 2, 1986, pp. 103–131.

International Search Report for PCT/US 01/14110, Jan. 2002.

* cited by examiner

Primary Examiner—Richard L. Raymond
(74) Attorney, Agent, or Firm—Alex Andrus

(57) ABSTRACT

Fluorescent, sulfonated 3,7-diamino-[8,9] benzophenoxazine dyes are provided that are especially useful for labelling biopolymers and other substrates. The dye-labelled conjugates can be used in a variety of contexts, including cell surface assays employing intact, live cells and in nucleic acid detection methods. The new dyes are water soluble and can be conjugated to a variety of substrates, such as polynucleotides, nucleosides, nucleotides, peptides, proteins, antibodies, carbohydrates, ligands, particles and surfaces.

41 Claims, 12 Drawing Sheets

6

↓ ClSO$_3$H / Na$_2$SO$_4$ / H$_2$O

7

↓ TSTU

8

C₂₀H₁₉N₃O₄S  Mass 397.1

C₃₀H₃₂N₄O₈S  Mass 608.2

C₂₈H₂₇N₃O₉S₂  Mass 613.1

C₃₂H₃₀N₄O₁₁S₂  Mass 710.1

$C_{28}H_{33}N_3O_3$ Mass 459.3

$C_{22}H_{17}N_3O$ Mass 339.1

$C_{30}H_{31}N_3O_3$ Mass 481.2

$C_{26}H_{29}N_3O_6S$ Mass 511.2

SULFONATED [8,9] BENZOPHENOXAZINE DYES AND THE USE OF THEIR LABELLED CONJUGATES

I. FIELD OF THE INVENTION

The present invention relates to sulfonated 3,7-diamino-[8,9]benzophenoxazine dye compounds and uses thereof.

II. BACKGROUND OF THE INVENTION

Fluorescent reagents enable life science research in many fields, including biological, biomedical, genetic, fermentation, aquaculture, agriculture, forensic and environmental applications. Fluorescent probes and stains identify biopolymers and detect particular biological components within and outside cells. A common example is the use of fluorescent-labelled antibodies to detect cell-surface receptors. Another example is the widespread use of gel electrophoresis for characterizing nucleic acids, one limitation of which is the sensitivity of the methods used to detect the nucleic acid bands.

Detection of biological analytes utilizing fluorescent labels eliminates the need for radioactive labels, thereby enhancing safety and diminishing the adverse environmental impact and costs associated with radioactive waste disposal. Examples of methods utilizing fluorescent detection methods include automated DNA sequencing, oligonucleotide probe methods, detection of polymerase-chain-reaction products, immunoassays, and the like. In the life and medical sciences, researchers and technicians often need to detect proteins, antigens, and other ligands on the surface of cells. Receptor based assays utilize labelled molecules, e.g. fluorescent labelled peptides, proteins, and antibodies to detect expressed proteins and other ligands.

Dyes that are generally applicable for staining or labelling biopolymers across a broad range of applications preferably have the following properties: (i) the dye-biopolymer conjugate or complex should produce a very high signal with low background so that small quantities of biopolymers can be sensitively detected in both cell-free and cell-based assays; and (ii) the conjugate or complex should be photostable so that the fluorescent signal may be observed, monitored and recorded without significant photo bleaching. For applications involving cell surface binding of dye-peptide or dye-antibody conjugates to membranes or cell surfaces, especially live cells, the dyes preferably (iii) have good water-solubility to achieve effective conjugate concentration and detection sensitivity and (iv) are non-toxic to living cells so as not to disrupt the normal metabolic processes of the cells or cause premature cell death.

While many dye compounds have found use as nucleic acid stains, most available dyes fluoresce in the green region of the visible spectrum. Green lasers are more expensive than red lasers and give higher background signals in live cell assays due to autofluorescence of cellular components and assay equipment. These higher background signals decrease the sensitivity of the assay. Moreover, many cellular components absorb green light, further reducing the sensitivity of the assay. Thus, sensitive dyes that are photostable, have excitation and emission maxima in the red region of the visible spectrum and that are water-soluble are highly desirable.

III. SUMMARY OF THE INVENTION

The present invention relates to a new class of sulfonated 3,7-diamino-[8,9]benzophenoxazine dyes which are useful, among other things, for labelling substrates for fluorescent detection. In one aspect, compounds of the invention emit light in the red region of the light spectrum, with excitation maxima typically 600 nm or greater. The compounds have excellent solubility in aqueous solutions and can enhance the water-solubility of molecules to which they are attached.

Generally, the present invention provides dye compounds comprising a 3,7-diamino-[8,9]benzophenoxazine structure which contains at least one sulfonate substituent. In one embodiment, the invention includes a dye compound defined by the formula (I):

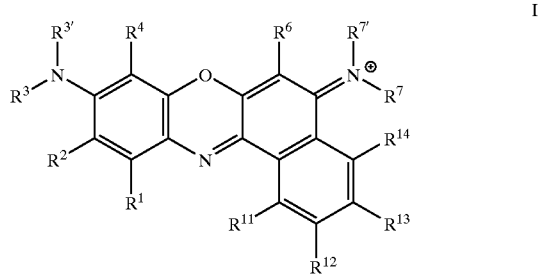

including any associated counter ions, wherein:

$R^1$, $R^2$, $R^4$, $R^6$, $R^{11}$, $R^{12}$, $R^{13}$ and $R^{14}$, when taken alone, are separately hydrogen, sulfonate, carboxylate, phosphonate, phosphate, halogen, $C_1$–$C_6$ alkyl, $C_1$–$C_6$ aminoalkyl, $C_5$–$C_{14}$ aryl, $C_5$–$C_{14}$ aryl substituted with one or more of the same or different W groups, —$OR^A$, —$SR^A$, —$NR^A R^B$, —CN, —$NO_2$, —$C(O)R^A$ or a reactive linking group;

$R^1$ when taken together with $R^2$ is $C_5$–$C_{14}$ aryleno or $C_5$–$C_{14}$ aryleno substituted with one or more of the same or different W groups;

$R^3$, $R^{3'}$, $R^7$ and $R^{7'}$, when taken alone, are separately hydrogen, a reactive linking group, an aliphatic cationic chain, $C_1$–$C_6$ alkyl or $C_5$–$C_{14}$ aryl;

$R^3$ when taken together with $R^{3'}$ is $C_2$–$C_8$ alkyldiyl;

$R^7$ when taken together with $R^{7'}$ is $C_2$–$C_8$ alkyldiyl;

$R^{11}$ and $R^{12}$, when taken together, are $C_5$–$C_{14}$ aryleno or $C_5$–$C_{14}$ aryleno substituted with one or more of the same or different W groups;

$R^{12}$ and $R^{13}$, when taken together, are $C_5$–$C_{14}$ aryleno or $C_5$–$C_{14}$ aryleno substituted with one or more of the same or different W groups;

$R^{13}$ and $R^{14}$, when taken together, are $C_5$–$C_{14}$ aryleno or $C_5$–$C_{14}$ aryleno substituted with one or more of the same or different W groups;

each W is independently hydrogen, sulfonate, carboxylate, phosphonate, phosphate, halogen, $C_1$–$C_6$ alkyl, —$OR^A$, —$SR^A$, —$NR^A R^B$, —CN, —$NO_2$ or —$C(O)R^A$; and each $R^A$ and each $R^B$ is independently hydrogen or $C_1$–$C_6$ alkyl;

with the proviso that at least one of $R^1$, $R^2$, $R^4$, $R^6$, $R^{11}$, $R^{12}$, $R^{13}$ and $R^{14}$ is sulfonate, or $R^{12}$ and $R^{13}$ taken together are benzo containing at least one sulfonate attached to the benzo ring, or at least one of $R^3$, $R^{3'}$, $R^7$ and $R^{7'}$ is $C_1$–$C_6$ alkylsulfonate or $C_4$–$C_{10}$ arylsulfonate.

The invention also includes a dye compound defined by the formula (II):

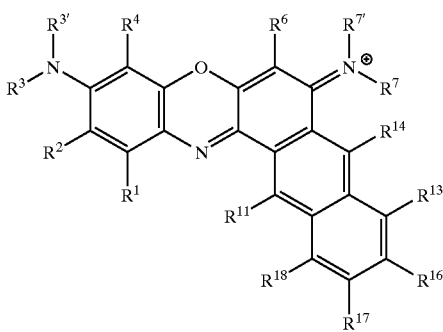

wherein $R^{15}$, $R^{16}$, $R^{17}$, and $R^{18}$ are separately hydrogen, sulfonate, carboxylate, phosphonate, phosphate, halogen, $C_1$–$C_6$ alkyl, $C_5$–$C_{14}$ aryl, $C_5$–$C_{14}$ aryl substituted with one or more of the same or different W groups, —$OR^A$, —$SR^A$, —$NR^A R^B$, —CN, —$NO_2$, —$C(O)R^A$ or a reactive linking group, wherein $R^A$ and $R^B$ are as defined above.

In one embodiment of formula I or formula II, a 5- to 7-member ring whose ring atoms are selected from carbon, nitrogen, oxygen, and sulfur is formed by $R^2$ and $R^3$ taken together with the C2-ring atom, C3 ring atom, and 3-nitrogen atom; or by $R^{3'}$ and $R^4$ taken together with the 3-nitrogen atom, C3-ring atom, and C4-ring atom; or by $R^6$ and $R^{7'}$ taken together with the C6-ring atom, C7-ring atom, and 7-nitrogen atom; or by $R^7$ and $R^{14}$ taken together with the 7-nitrogen atom, C7-ring atom, C8-ring atom, and C14-ring atom. The 5- to 7-member ring may optionally include a gem-disubstituted carbon atom. For example, the gem disubstituted carbon atom can be substituted with two $C_1$–$C_6$ alkyl groups which may be the same or different, such as methyl.

In further embodiments with reference to formulas I and II above, $R^1$, $R^2$, $R^4$ and $R^6$ are each hydrogen; or $R^3$ and $R^{3'}$ are each independently $C_1$–$C_3$ alkyl; or $R^1$ and $R^2$ together are [1,2]benzeno, [1,2]naphthaleno or [2,3]naphthaleno; or $R^{11}$, $R^{12}$, $R^{13}$ and $R^{14}$ are each hydrogen; or in formula I, $R^{11}$ and $R^{12}$ together or $R^{12}$ and $R^{13}$ together or $R^{13}$ and $R^{14}$ together are [1,2]benzeno.

In another embodiment, the aliphatic cationic chain is —$(CH_2)_n$—$NR_2$, —$(CH_2)_n$—$^+NR_3$, —$(CH_2)_n$—$^+NR_2$—$(CH_2)_n$—$NR_2$ or —$(CH_2)_n$—$^+NR_2$—$(CH_2)_n$—$^+NR_3$, each n is independently an integer from 2 to 3, and each occurrence of R is independently selected from hydrogen and $C_1$–$C_6$ alkyl.

In certain preferred embodiments, alkylsulfonate is —$(CH_2)_n$—$SO_3H$, and n is an integer from 1 to 6, or arylsulfonate is:

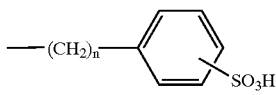

wherein n is 0 or 1.

The reactive linking group, when present, is preferably succinimidyl ester, isothiocyanate, sulfonyl chloride, 2,6-dichlorotriazinyl, pentafluorophenyl ester, phosphoramidite, maleimide, haloacetyl, or iodoacetamide, although other linking groups can also be used. In more specific embodiments, the reactive linking group is N-hydroxysuccinimide (especially useful for conjugation with a polypeptide) or a phosphoramidite (a preferred group for conjugation to a nucleoside, nucleotide, or polynucleotide).

The compounds of the present invention can be conjugated with a variety of substrate moieties, such as polynucleotides, nucleotides, nucleosides, polypeptides, carbohydrates, ligands, particles, and surfaces, for example. In one embodiment, the substrate is particle, such as a nanoparticle, microsphere, bead, or liposome. In another embodiment, the substrate is a surface, such is a glass surface. Accordingly, the invention includes such conjugates and methods of preparing them.

The invention further includes an energy transfer dye compound comprising: a donor compound which is linked by a linker to an acceptor compound, wherein the donor compound is capable of emitting excitation energy in response to absorption of light at a first wavelength, and the acceptor compound is capable of fluorescing at a second wavelength upon absorbing the excitation energy emitted by the donor compound, wherein at least one of the donor compound and the acceptor compound is a compound in accordance with the present invention.

The invention also includes a phosphoramidite compound defined by the formula (III):

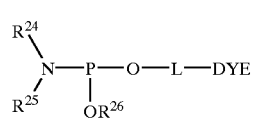

wherein DYE is a dye compound or energy transfer dye compound of the type described above; L is a linker; $R^{24}$ and $R^{25}$ taken separately are $C_1$–$C_{12}$ alkyl, $C_4$–$C_{10}$ aryl, or cycloalkyl containing up to 10 carbon atoms; or $R^{24}$ and $R^{25}$ taken together with the phosphoramidite nitrogen atom form a saturated nitrogen heterocycle; and $R^{26}$ is a phosphite ester protecting group. In one embodiment, $R^{26}$ is methyl, 2-cyanoethyl, or 2-(4-nitrophenyl)ethyl. In another embodiment, $R^{24}$ and $R^{25}$ are each isopropyl. In another embodiment, $R^{24}$ and $R^{25}$ taken together are morpholino. In another embodiment, L is $C_1$–$C_{12}$ alkyldiyl. In another embodiment, L is attached to the 3-nitrogen atom or the 7-nitrogen atom of the 3,7-diamino-[8,9]benzophenoxazine structure. In one exemplary embodiment, $R^{24}$ and $R^{25}$ are each isopropyl, $R^{26}$ is cyanoethyl, and L-DYE is defined by the formula:

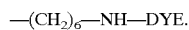

The invention also provides a nucleoside or nucleotide compound defined by the formula (IV):

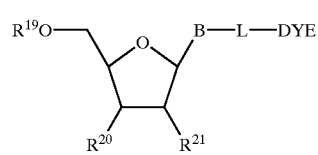

wherein DYE is a dye compound or energy transfer dye compound of the type discussed above; L is a linker; B is a nucleobase; $R^{19}$ is H, monophosphate, diphosphate, triphosphate, or phosphate analog thereof; and $R^{20}$ and $R^{21}$, when taken alone, are each independently H, HO, F, a phosphoramidite group, or a moiety which blocks polymerase-mediated polymerization, or when taken together, form 2'-3'-didehydroribose. In one set of embodiments, B is uracil, thymine, cytosine, adenine, 7-deazaadenine, guanine, 7-deazaguanosine, 7-deaza-8- azaguanine, or 7-deaza-8-azaadenine. In another embodiment, the compound is enzymatically incorporatable. In another embodiment, the compound is a terminator. In one terminator embodiment, $R^{19}$ is triphosphate, α-thiotriphosphate, or triphosphate ester analog; and $R^{20}$ and $R^{21}$, when taken alone, are each independently H, F, or a moiety which blocks polymerase-mediated polymerization, or when taken together, form 2'-3'-didehydroribose. In another embodiment, the nucleoside or nucleotide is enzymatically extendable.

In another aspect, the invention includes a polynucleotide of the formula (V):

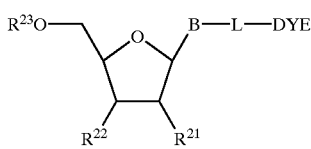

V wherein the polynucleotide comprises two or more nucleotides; DYE is a dye compound or energy transfer dye compound of the type described above; L is a linker; B is a nucleobase; $R^{21}$ is H, OH, halide, azide, amine, $C_1$–$C_6$ aminoalkyl, $C_1$–$C_6$ alkyl, allyl, $C_1$–$C_6$ alkoxy; —$OCH_3$, or —$OCH_2CH$=$CH_2$; and $R^{22}$ and $R^{23}$ are independently H, phosphate, internucleotide phosphodiester, or internucleotide analog.

The invention also includes a polynucleotide of the formula (VI):

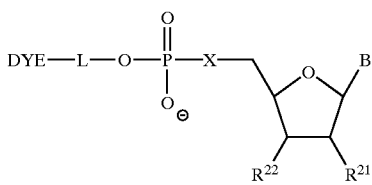

VI which comprises two or more nucleotides; wherein DYE is a dye compound or energy transfer dye compound of the type described above; L is a linker; X is O, NH, or S; B is a nucleobase; $R^{21}$ is H, OH, halide, azide, amine, $C_1$–$C_6$ aminoalkyl, $C_1$–$C_6$ alkyl, allyl, $C_1$–$C_6$ alkoxy; —$OCH_3$, or —$OCH_2CH$=$CH_2$; and $R^{22}$ is internucleotide phosphodiester or internucleotide analog. In one embodiment, L is $C_1$–$C_{12}$ alkyldiyl. In another embodiment, L comprises —$(CH_2CH_2O)_n$—, and n is 1 to 100.

The invention also includes a conjugate defined by the formula:

P—L—DYE wherein P is a polypeptide; L is a linker; and DYE is a dye compound or energy transfer dye compound of the type described above. In one embodiment, L is an amide bond. In another embodiment, L is attached to P through a carboxyl terminus, an amino terminus, a lysine sidechain, an aspartic acid sidechain, or a glutamic acid sidechain. In further embodiments, P is streptavidin, a caspase-cleavage substrate, or an antibody.

In another aspect, the invention includes a method of detecting a cell surface receptor comprising the steps of binding a P—L—DYE conjugate such as just described to a surface receptor of a cell and detecting a fluorescence signal from bound conjugate.

In another aspect, the invention includes a method of bead-based immunocapture comprising the steps of binding a P—L—DYE conjugate such as just described to an antibody-coated bead and detecting a fluorescence signal from bound conjugate.

In another aspect, the invention includes a method of synthesizing a labelled polynucleotide comprising coupling a phosphoramidite compound such as described above to a polynucleotide bound to a solid support. In one embodiment, such a method may include coupling a nucleoside phosphoramidite to a solid support-bound dye compound or a energy transfer compound such as described above, to synthesize a labelled polynucleotide.

In another aspect, the invention includes a method of generating a labelled primer extension product, comprising the step of enzymatically extending a primer-target hybrid in the presence of (i) a mixture of enzymatically-extendable nucleotides capable of supporting continuous primer extension and (ii) a terminator, wherein the primer or terminator is labelled with a dye compound or energy transfer compound such as described above.

In another aspect, the invention includes a ligation method comprising annealing two polynucleotide probes to a target polynucleotide sequence, and forming a phosphodiester bond between a 5' terminus of one of the probes and the 3' terminus of the other probe, wherein one or both probes contain a dye compound or energy transfer compound such as described above.

In another aspect, the invention includes a method of fragment analysis comprising the steps of subjecting a plurality of polynucleotide fragments to a size-dependent separation process, wherein the fragments contain a dye compound or energy transfer compound such as described above, and detecting the labelled polynucleotide fragment after initiating the separation process.

In another aspect, the invention includes an amplification method comprising the steps of: annealing two or more primers to a target DNA sequence and extending the primers by polymerase-mediated extension in the presence of one or more enzymatically-extendable nucleotides. The nucleotides may be labelled with a dye of the present invention. The amplification method may further comprise annealing a fluorescent dye-quencher probe to the target DNA sequence, wherein the probe contains compound of the present invention.

The invention also provides kits containing dye compounds of the invention (in free or conjugate form) and one or more other components that may be used to label substrates, conduct tests, or the like. For example, such kits may be useful for labelling oligonucleotides, generating labelled primer extension products, immunocapture assays, and cell receptor assays.

IV. BRIEF DESCRIPTION OF THE DRAWINGS

Figure 5:
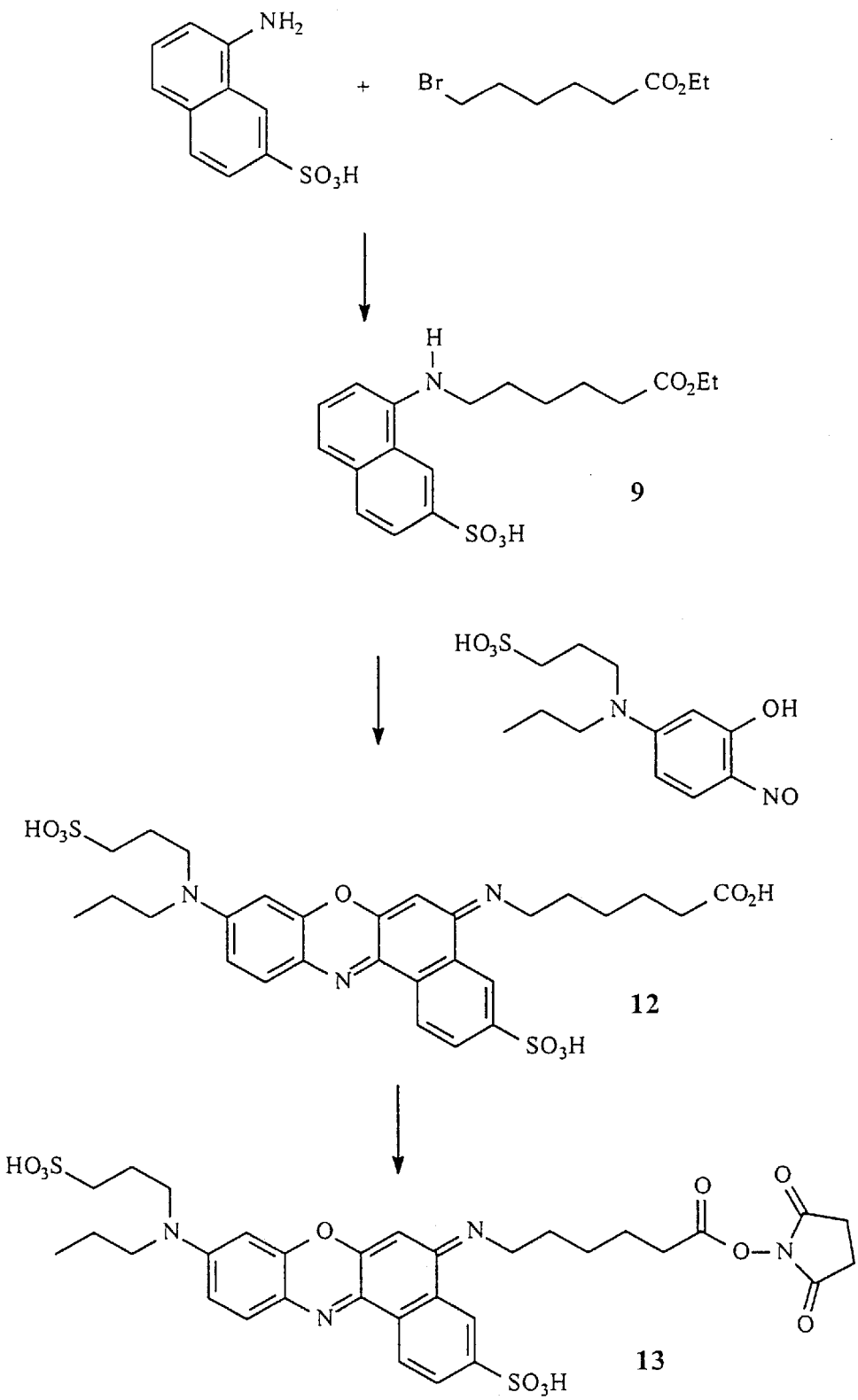

FIG. 5 shows alkylation to form 9, cyclization to form 12, and activation to form NHS ester 13.

Figure 6:
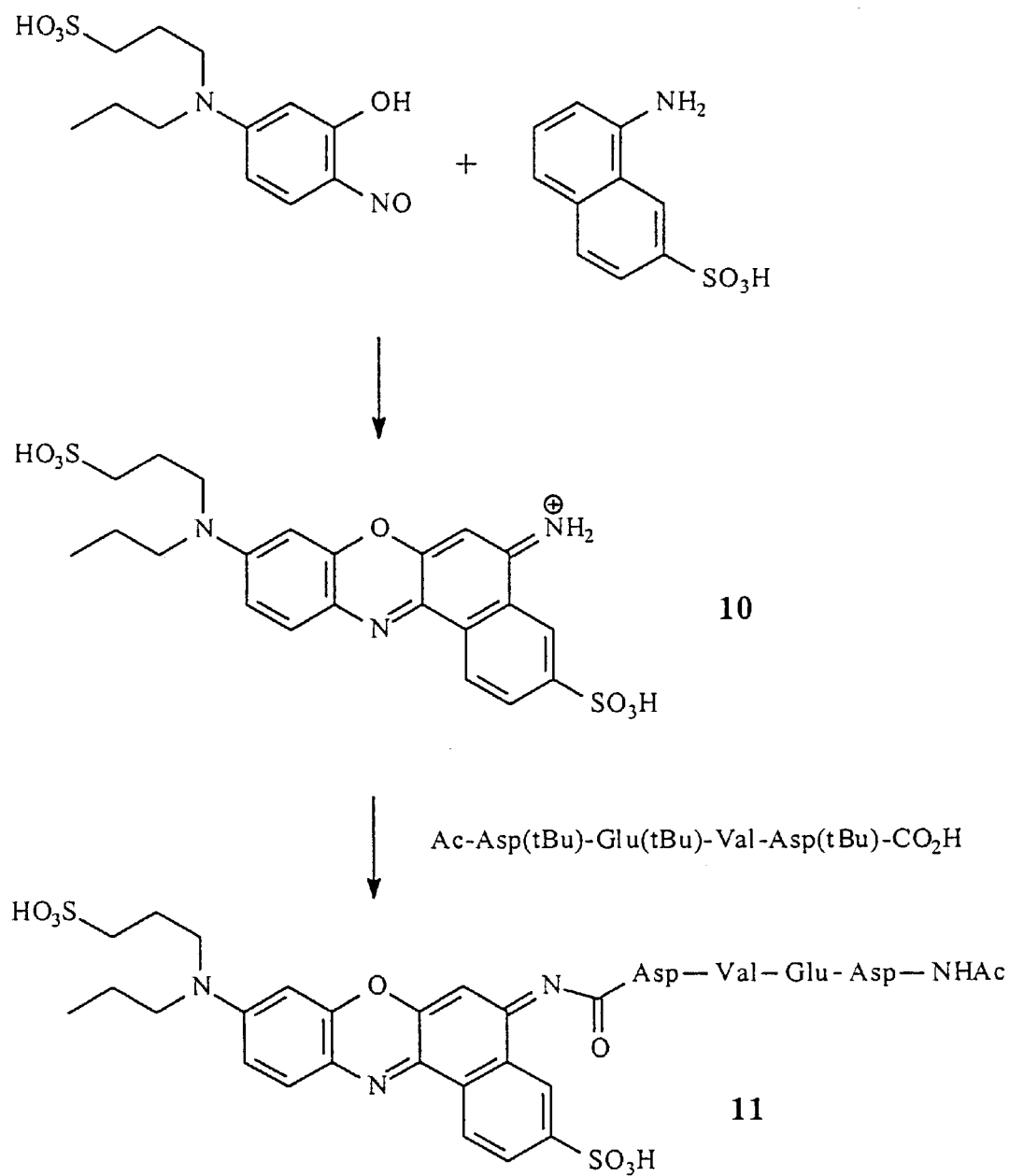

FIG. 6 shows formation of an exemplary protected DEVD peptide conjugate 11.

Figure 7:
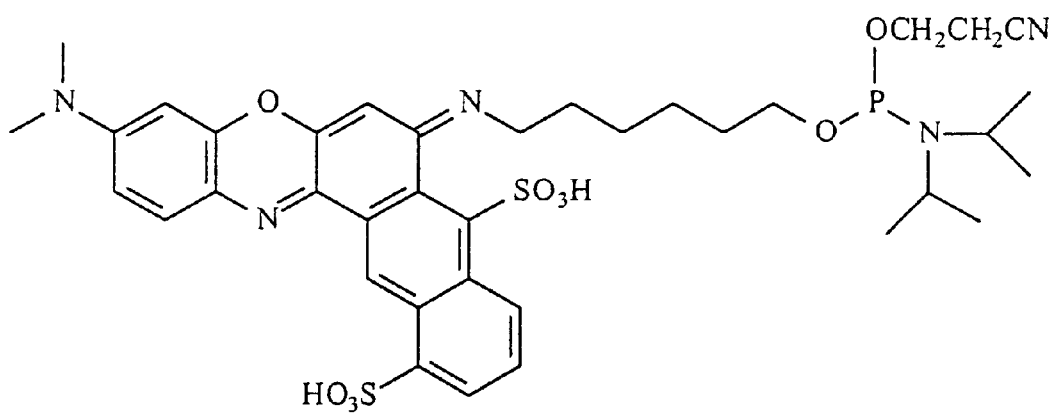
Figure 7:
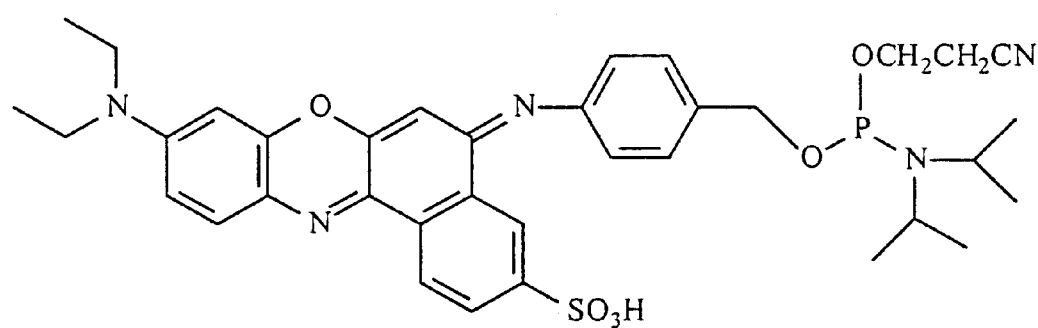

FIG. 7 shows exemplary phosphoramidite compounds of the invention.

Figure 8:
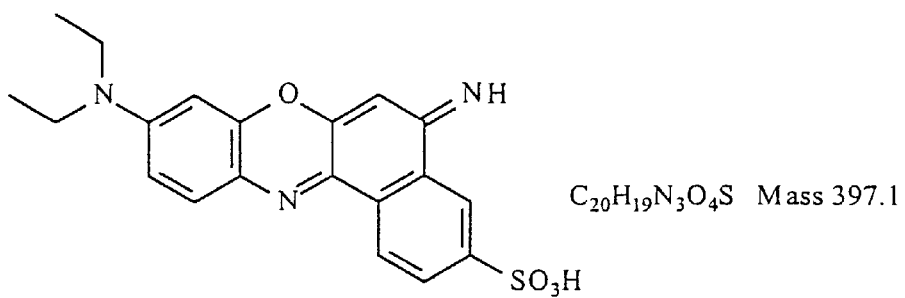
Figure 8:
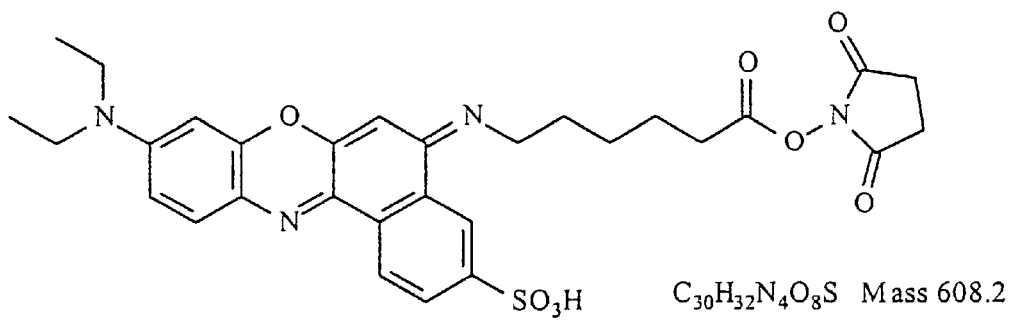
Figure 8:
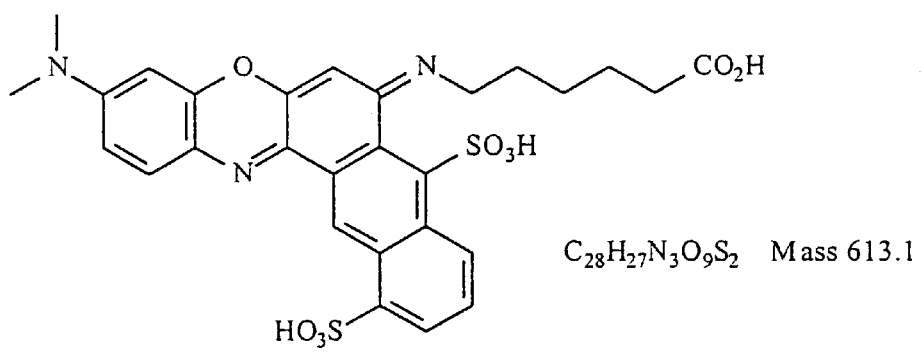
Figure 8:
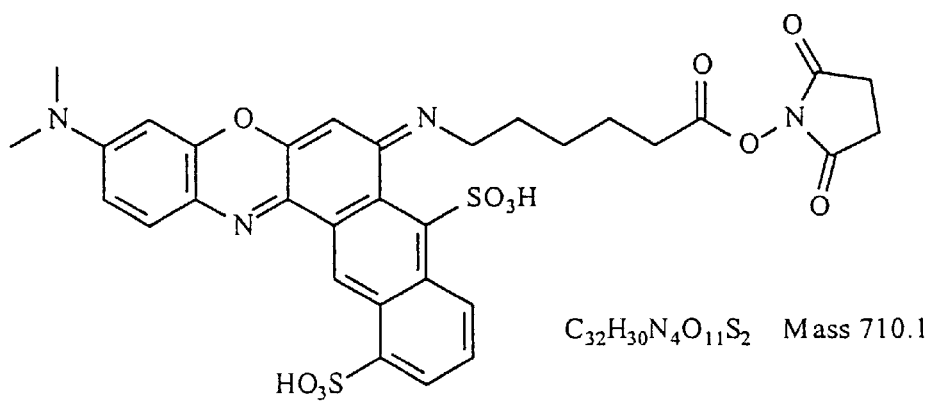

FIG. 8 shows mass spectrometry results for certain exemplary compounds of the invention.

Figure 9:
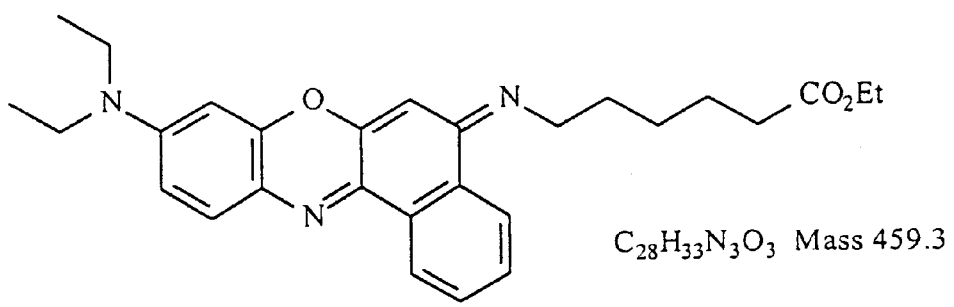
Figure 9:
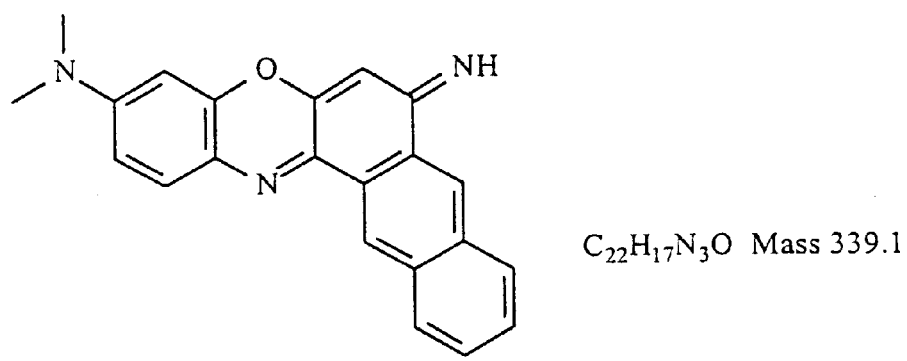
Figure 9:
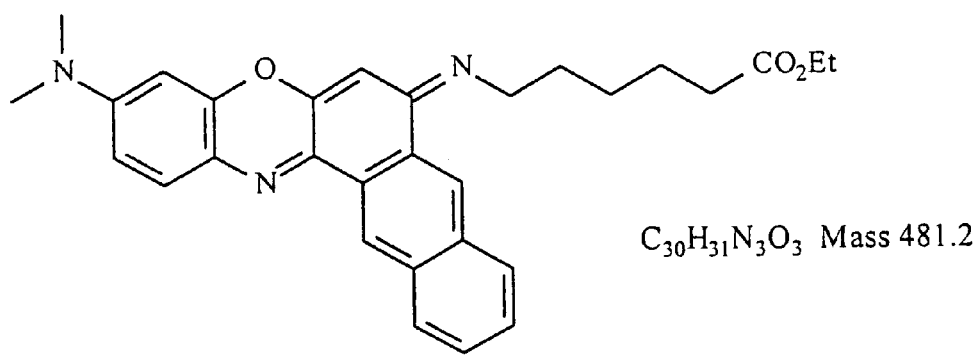
Figure 9:
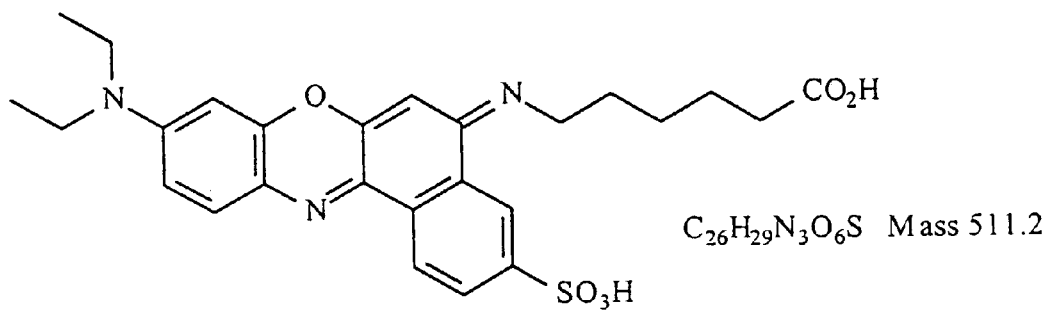

FIG. 9 shows mass spectroscopy results for certain intermediate compounds.

Figure 10:
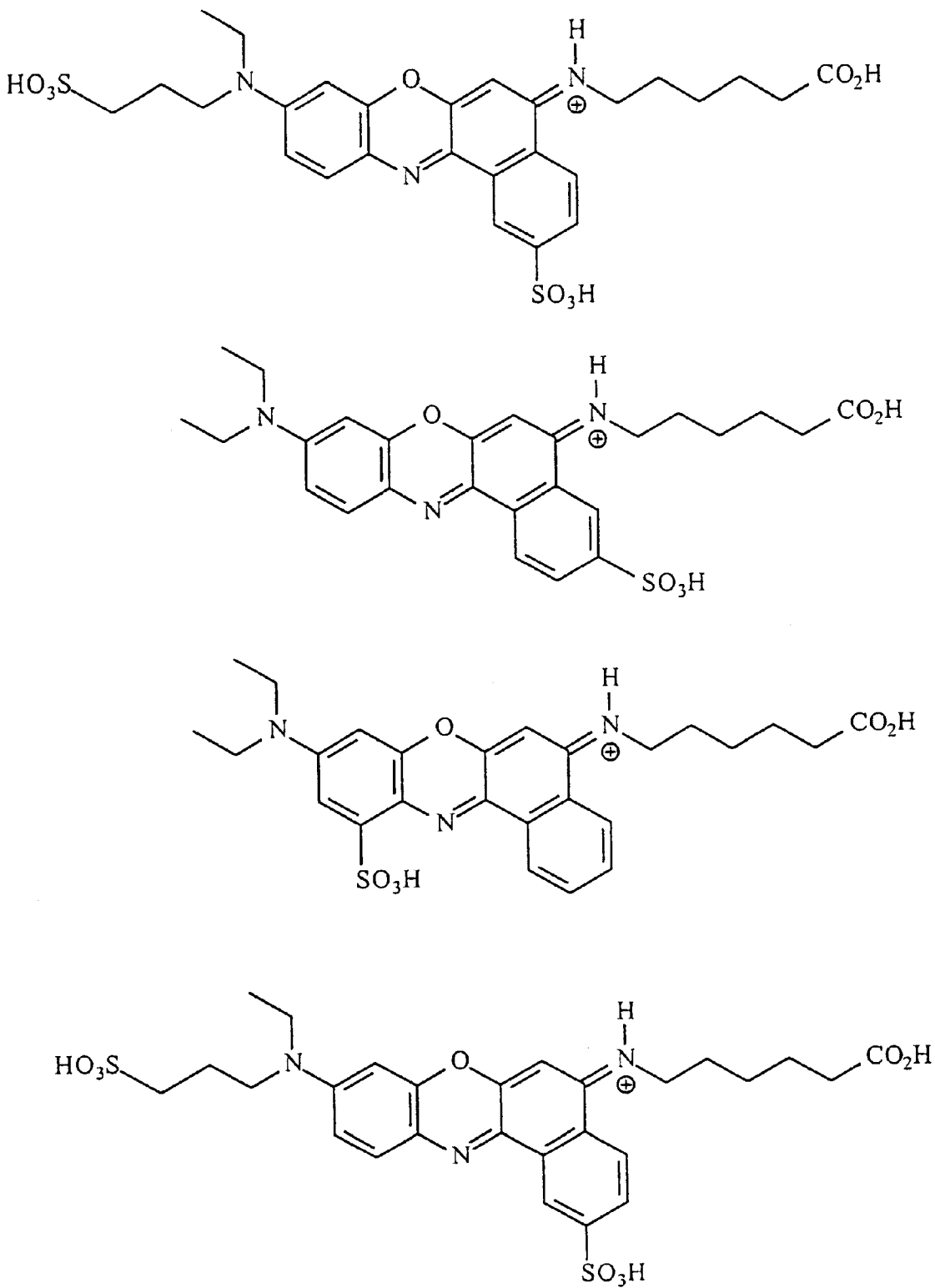

FIG. 10 shows certain exemplary compounds of the invention.

Figure 11A:
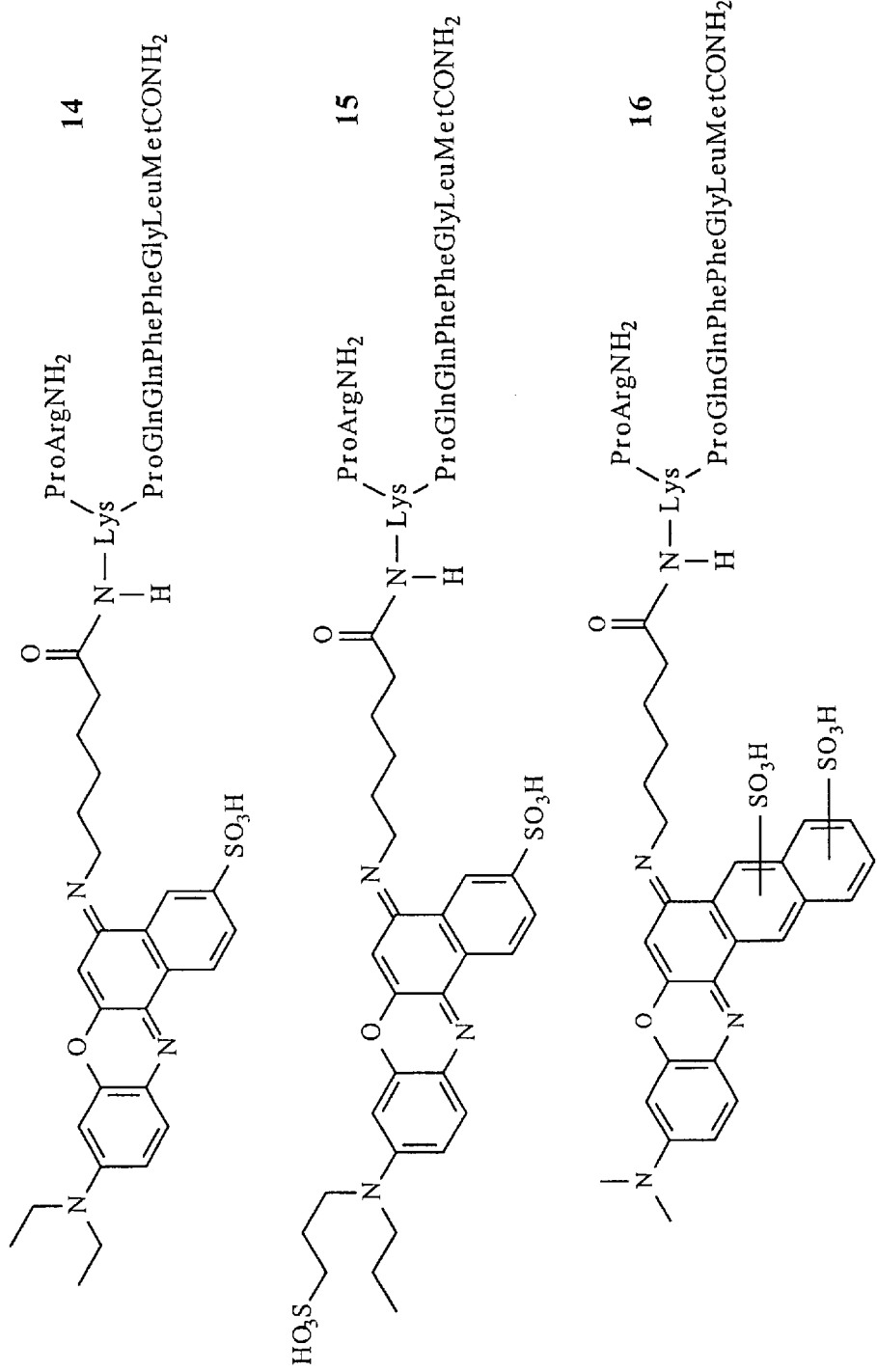

FIGS. 11A and B shows five exemplary polypeptide-dye conjugates 14–18 in accordance with the invention.

V. DETAILED DESCRIPTION

Reference will now be made in detail to embodiments of the invention, examples of which are illustrated in the accompanying drawings. While the invention will be described in conjunction with the preferred embodiments, it will be understood that they are not intended to limit the invention to those embodiments. On the contrary, the invention is intended to cover all alternatives, modifications, and equivalents, which may be included within the invention.

V.1 Definitions

For purposes of the present application, the positions of the [8,9]benzophenoxazine ring system for the compounds of the invention are numbered as follows:

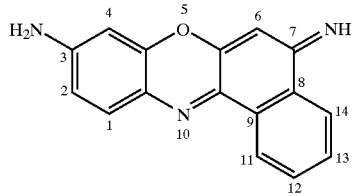

As used herein, the following terms are intended to have the following meanings:

"Alkyl" means a saturated or unsaturated, straight-chain, branched, or cyclic hydrocarbon radical derived by the removal of one hydrogen atom from a single carbon atom of a parent alkane, alkene, or alkyne. Typical alkyl groups include, but are not limited to, methyl, ethyl, propyl, butyl, and the like. Typical alkyl groups include, but are not limited to, methyl (—$CH_3$); ethyls such as ethanyl (—$CH_2$—$CH_3$), ethenyl (—CH=$CH_2$), ethynyl (—C≡CH); propyls such as propan-1-yl (—$CH_2$—$CH_2$—$CH_3$), propan-2-yl, cyclopropan-1-yl, prop-1-en-1-yl (—CH=CH—$CH_2$), prop-1-en-2-yl, prop-2-en-1-yl (—$CH_2$—CH=$CH_2$), prop-2-en-2-yl, cycloprop-1-en-1-yl; cycloprop-2-en-1-yl, prop-1-yn-1-yl (—C≡C—$CH_3$), prop-2-yn-1-yl (—$CH_2$—C≡CH), etc.; butyls such as butan-1-yl(—$CH_2$—$CH_2$—$CH_2$—$CH_3$), butan-2-yl, cyclobutan-1-yl, but-1-en-1-yl (—CH=$CH_2$—$CH_2$—$CH_3$), but-1-en-2-yl, but-2-en-1-yl (—$CH_2$—CH=$CH_2$—$CH_3$), but-2-en-2-yl, buta-1,3-dien-1-yl (—CH=CH—CH=$CH_2$), buta-1,3-dien-2-yl, cyclobut-1-en-1-yl, cyclobut-1-en-3-yl, cyclobuta-1,3-dien-1-yl, but-1-yn-1-yl (—C≡$CH_2$—$CH_3$), but-1-yn-3-yl, but-3-yn-1-yl (—$CH_2$—$CH_2$—C≡CH), etc.; and the like. In preferred embodiments, the alkyl groups are ($C_1$–$C_6$) alkyl, with ($C_1$–$C_3$) being particularly preferred.

"Alkoxy" means —OR where R is ($C_1$–$C_6$) alkyl.

"Aminoalkyl" means —$RNH_2$ where R is ($C_1$–$C_6$) alkyl.

"Alkyldiyl" means a saturated or unsaturated, branched, straight chain or cyclic hydrocarbon radical of 1–12 carbon atoms and having two monovalent radical centers derived by the removal of two hydrogen atoms from the same or two different carbon atoms of a parent alkane, alkene or alkyne. Typical alkyldiyl radicals include, but are not limited to, methano (—$CH_2$—); 1,2-ethyldiyl; 1,3-propyldiyl; 1,4-butyldiyl; and the like.

"Aryl" refers to a monovalent aromatic hydrocarbon radical of 6–20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Aryldiyl" refers to an unsaturated cyclic or polycyclic hydrocarbon radical of 6–20 carbon atoms having a conjugated resonance electron system and at least two monovalent radical centers derived by the removal of two hydrogen atoms from two different carbon atoms of a parent aryl compound.

"Aryleno" means a divalent bridge radical having two adjacent monovalent radical centers derived by the removal of one hydrogen atom from each of two adjacent carbon atoms of a parent aromatic ring system. Attaching an aryleno bridge radical, e.g. benzeno, to a parent aromatic ring system, e.g. benzene, results in a fused aromatic ring system, e.g. naphthalene. The bridge is assumed to have the maximum number of non-cumulative double bonds consistent with its attachment to the resultant fused ring system. When an aryleno substituent is formed by taking together two adjacent substituents on a structure that includes alternative substituents, to avoid double-counting carbon atoms, the carbon atoms of the aryleno bridge replace the bridging carbon atoms of the structure.

As an example, consider the structure:

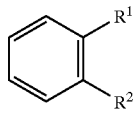

When $R^1$ and $R^2$ are each hydrogen, the resultant compound is benzene. When $R^1$ taken together with $R^2$ is $C_6$ aryleno (benzeno), the resultant compound is naphthalene. When $R^1$ taken together with $R^2$ is $C_{10}$ aryleno (naphthaleno), the resultant compound is anthracene or phenanthrene. Where a specific connectivity is intended, the involved bridging carbon atoms (of the aryleno bridge) are denoted in brackets, e.g., [1,2]benzeno ([1,2]benzo), [1,2]naphthaleno, [2,3]naphthaleno, etc.

"Nucleobase" means a nitrogen-containing heterocyclic moiety capable of forming Watson-Crick hydrogen bonds in pairing with a complementary nucleobase or nucleobase analog, e.g. a purine, a 7-deazapurine, or a pyrimidine. Typical nucleobases are the naturally occurring nucleobases adenine, guanine, cytosine, uracil, thymine, and analogs of the naturally occurring nucleobases, e.g. 7-deazaadenine, 7-deazaguanine, 7-deaza-8-azaguanine, 7-deaza-8-azaadenine, inosine, nebularine, nitropyrrole, nitroindole, 2-amino-purine, 2,6-diamino-purine, hypoxanthine, pseudouridine, pseudocytidine, pseudoisocytidine, 5-propynyl-cytidine, isocytidine, isoguanine, 7-deazaguanine, 2-thio-pyrimidine, 6-thio-guanine, 4-thio-thymine, 4-thio-uracil, $O^6$-methyl-guanine, $N^6$-methyladenine, $O^4$-methyl-thymine, 5,6-dihydrothymine, 5,6-dihydrouracil, 4-methyl-indole, and ethenoadenine (Fasman (1989) *Practical Handbook of Biochemistry and Molecular Biology*, pp. 385–394, CRC Press, Boca Raton, Fla.).

"Nucleoside" refers to a compound consisting of a nucleobase linked to the C-1' carbon of a ribose sugar. The ribose may be substituted or unsubstituted. Substituted ribose sugars include, but are not limited to, those riboses in which one or more of the carbon atoms, preferably the 3'-carbon atom, is substituted with one or more of the same or different —R, —OR, —NRR or halogen groups, where each R is independently —H, ($C_1$–$C_6$) alkyl or ($C_5$–$C_{14}$) aryl. Particularly preferred riboses are ribose, 2'-deoxyribose, 2',3'-dideoxyribose, 3'-haloribose, 3'-fluororibose, 3'-chlororibose, and 3'-alkylribose. When the nucleobase is A or G, the ribose sugar is attached to the $N^9$-position of the nucleobase. When the nucleobase is C, T or U, the pentose sugar is attached to the $N^1$-position of the nucleobase (Kornberg and Baker, (1992) DNA *Replication*, $2^{nd}$ Ed., Freeman, San Francisco, Calif.

"Nucleotide" refers to a phosphate ester of a nucleoside, as a monomer unit or within a nucleic acid. Nucleotides are sometimes denoted as "NTP", or "dNTP" and "ddNTP" to particularly point out the structural features of the ribose sugar. "Nucleotide 5'-triphosphate" refers to a nucleotide with a triphosphate ester group at the 5' position. The triphosphate ester group may include sulfur substitutions for the various oxygens, e.g. α-thio-nucleotide 5'-triphosphates.

As used herein, the terms "polynucleotide" or "oligonucleotide" encompass any polymer sequence comprised of two or more contiguous nucleosides, nucleotides or analogs thereof. "Oligonucleotide" and "polynucleotide" are used interchangeably and mean single-stranded and double-stranded polymers of nucleotide monomers, including 2'-deoxyribonucleotides (DNA) and ribonucleotides (RNA). An polynucleotide may be composed entirely of deoxyribonucleotides, entirely of ribonucleotides, or chimeric mixtures thereof, linked by internucleotide phosphodiester bond linkages, or internucleotide analogs, and associated counter ions, e.g., $H^+$, $NH_4^+$, trialkylammonium, $Mg^{2+}$, $Na^+$ and the like. Polynucleotides may be comprised of nucleobase and sugar analogs. Polynucleotides typically range in size from a few monomeric units, e.g. 5–40 when they are frequently referred to as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

"Polypeptide" means a peptide or a protein, e.g. an antibody or an enzyme.

"Attachment site" refers to a site on a moiety, e.g. a dye, a peptide, or an oligonucleotide, to which is covalently attached a linker.

"Linker" refers to a chemical moiety comprising a covalent bond or a chain of atoms that covalently attaches a dye to a substrate, e.g. a polynucleotide, or one dye to another.

"Reactive linking group" refers to a chemically reactive substituent or moiety, e.g. a nucleophile or electrophile, capable of reacting with another molecule to form a covalent bond.

"Heterocycle" refers to a molecule with a ring system in which one or more ring atoms is a heteroatom, e.g. nitrogen, oxygen, and sulfur (as opposed to carbon).

"Enzymatically extendable" refers to a nucleotide which is capable of: (i) being enzymatically incorporated onto the terminus of a polynucleotide chain through the action of a polymerase enzyme, and (ii) capable of supporting continuous primer extension.

"Enzymatically incorporatable" refers to a nucleotide which is capable of being enzymatically incorporated onto the terminus of a polynucleotide chain through the action of a polymerase enzyme.

"Terminator" means an enzymatically incorporatable nucleotide which prevents subsequent incorporations of nucleotides to the resulting polynucleotide chain and thereby halt polymerase extension. Typical terminators lack a 3'-hydroxyl substituent and include 2',3'-dideoxyribose, 2',3'-didehydroribose, and 2',3'-dideoxy, 3'-haloribose, e.g. 3'-fluoro. Alternatively, a ribofuranose analog may be used, such as arabinose. Exemplary nucleotide terminators include 2',3'-dideoxy-β-D-ribofuranosyl, β-D-arabinofuranosyl, 3'-deoxy-β-D-arabinofuranosyl, 3'-amino-2',3'-dideoxy-β-D-ribofuranosyl, and 2',3'-dideoxy-3'-fluoro-β-D-ribofuranosyl (Chidgeavadze. (1984) Nucleic Acids Res., 12: 1671–1686; and Chidgeavadze. (1985) FEB. Lett., 183: 275–278). Nucleotide terminators also include reversible nucleotide terminators (Metzker (1994) Nucleic Acids Res., 22(20): 4259).

"Substrate" is an entity to which a dye compound of the present invention can be attached. Substrates include, but are not limited to a (i) polynucleotide, (ii) nucleoside and nucleotide, (iii) peptide and protein, (iv) carbohydrate, (v) ligand, and (vi) any analog of the preceding (i) to (v).

"Internucleotide analog" means a phosphate ester analog such as an alkylphosphonate (e.g., $C_1$–$C_4$ alkylphosphonate such as methylphosphonate), phosphoramidate, alkylphosphotriester (e.g., $C_1$–$C_4$ alkylphosphotriester such as methylphosphotriester), phosphorothioate, and phosphorodithioate. Internucleotide analogs include also non-phosphate analogs wherein the sugar/phosphate subunit is replaced by an amide linkage, such as a 2-aminoethylglycine unit (e.g., PNA; see Nielsen, "Sequence-selective recognition of DNA by strand displacement with a thymidine-substituted polyamide", Science 254:1497–1500 (1991)).

"Target sequence" means a polynucleotide sequence that is the subject of hybridization with a complementary polynucleotide. The sequence can be composed of DNA, RNA, an analog thereof, including combinations thereof.

"Spectrally Resolvable" means, in reference to a set of fluorescent dyes, that the fluorescence emission bands of the respective dyes are sufficiently distinct, i.e., sufficiently non-overlapping, that the dyes, either alone or when conjugated to other compounds (labelled), are distinguishable from one another on the basis of their fluorescence signals using standard photodetection systems such as photodetectors employing a series of band pass filters and photomultiplier tubes, charged-coupled devices (CCD), spectrographs, etc. (Wheeless et al., (1985) *Flow Cytometry: Instrumentation and Data Analysis*, pp. 21–76, Academic Press, New York). Preferably, all of the dyes comprising a spectrally resolvable set of dyes are excitable by a single light source.

"Mobility-Matched" refers to a set of fluorescent dyes that, when used to label polynucleotides of equal lengths, yields differentially labelled polynucleotides having substantially similar electrophoretic mobilities. Typically, the relative electrophoretic mobilities of polynucleotides labelled with a set of mobility-matched dyes will vary by less than about one-half nucleotide. Preferably, the mobility-matched dyes are spectrally resolvable, as previously defined.

V.2 Dye Compounds and Synthesis

The compounds of the present invention can be prepared by any suitable method available in the art. Exemplary methods for preparing a variety of different sulfonated dye compounds of the invention can be found in the Example section below, and as discussed in greater detail below.

Figure 1:
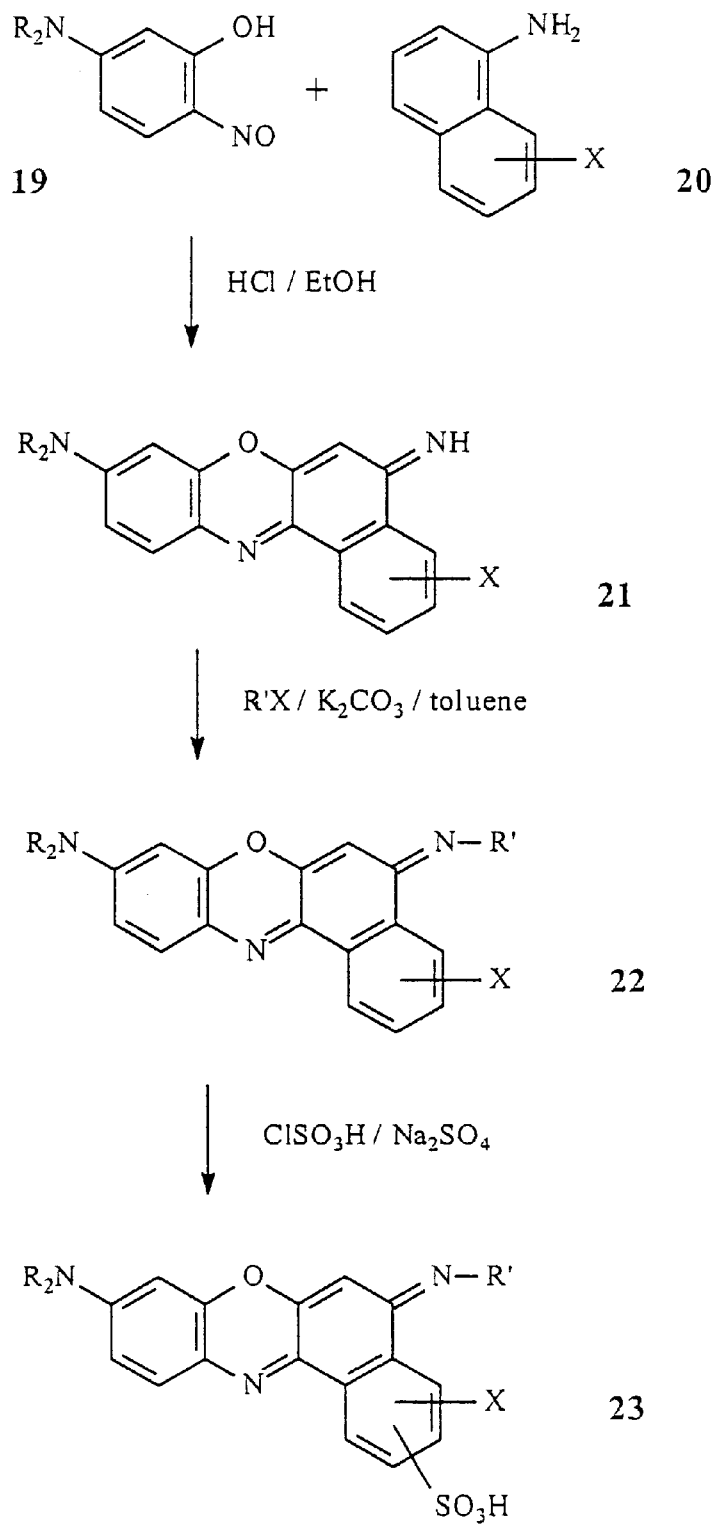
FIG. 1 shows a general synthetic route for preparing compounds in accordance with the invention.

The sulfonated 3,7-diamino-[8,9]benzophenoxazine dyes of the invention can be conveniently synthesized from precursors, such as illustrated in FIG. 1. An exemplary synthetic route starts by cyclization of a 2-nitroso, 5-aminophenol compound 19 and an equivalent of a 1-aminonaphthalene compound 20 each at final concentrations from 0.5 mM to 5 mM in ethanol, under acidic conditions, e.g. 0.1 to 0.5 M hydrochloric acid. The mixture is refluxed for 2 to 50 hours. After cooling, the solvents are evaporated, and the cyclized product 21 may be purified by crystallization and filtration or by reverse-phased HPLC. Either or both of the reactants 19 and 20 can be aryl-substituted with substituents X, e.g. sulfonate, as described. Alternatively, the sulfonate group can be introduced by sulfonation after the cyclization. The amino group of the 5-aminophenol compound 19 may bear alkyl groups, e.g. alkylsulfonate, arylsulfonate or other groups as shown in formula I. Alternatively, the 3,7-diamino-[8,9] benzophenoxazine ring structure can be synthesized by following the methods of Ottawa, "Process for the manufacture of basic oxazine dyestuffs", U.S. Pat. No. 3,655,601, where the nitroso functionality is formed in situ. Also, the 3-amino and 7-amino groups can be formed on the [8,9] benzophenoxazine ring structure by reaction with aryl azide reagents under light or heat, according to VanAllan, (1969) "The reaction of 12H-benzo[a]phenothiazine and 12H-benzo[b]phenoxazine with certain heterocyclic azides", Jour. Org. Chem. 34:1691–94.

The C3 and C7 primary or secondary amino groups can be alkylated under typical conditions to give various substituents. FIG. 1 shows an example of alkylation of the C7 amino group of 21 with an alkylating agent, e.g. bromoalkyl, halo-benzyl, or other electrophilic reagent gives the C7 amino alkylated product 22, following the general method of Briggs, (1997) "Synthesis of functionalised fluorescent dyes and their coupling to amines and amino acids", J. Chem. Soc., Perkin Trans. 1, 1051–58. Typically, the alkylation reaction is conducted under heterogeneous conditions, with a relatively insoluble base, e.g. potassium carbonate or sodium carbonate, in a solvent, e.g. toluene, dimethylformamide, acetonitrile, or tetrahydrofuran. The reaction may be heated to reflux temperatures to effect complete reaction. The alkylating reagents may include functionality convertible to reactive linking groups. Where the alkylating reagent contains a base sensitive functional group, e.g. ester, the base may be non-nucleophilic, e.g. Example 9.

The fused [8,9] benzo ring may be sulfonated with chlorosulfonic acid and sodium sulfate in methylene chloride, or another suitable solvent. Alternatively, the sulfonation may be conducted in neat chlorosulfonic acid. The resulting aryl sulfonyl chloride is hydrolyzed with water to the aryl sulfonate product. Aryl sulfonation of the phenol or naphthalene intermediates, or the cyclized product, may also be carried out in fuming sulfuric acid, $SO_3/H_2SO_4$ (Stewart "Aminonaphthalimide dyes for intracellular labelling", U.S. Pat. No. 4,473,693). Sulfonation may occur at one or more of several aryl positions to give a sulfonated [8,9] benzophenoxazine dye 23 (FIG. 1). The particular isomer may be determined by conventional analytical techniques, e.g. NMR, and purified from other isomers by reverse-phase HPLC. The number of resulting sulfonate groups may be determined by mass spectroscopy.

The synthetic route may entail sulfonation of a naphthyl amine compound, followed by alkylation, e.g. 9 in FIG. 5. Ring cyclization with a nitroso, aminophenol compound gives a dye of the invention, e.g. 12. Alternatively, cyclization of a primary amino, sulfonate naphthyl compound gives, e.g. 10 (FIG. 6). The C7 amino group may be acylated with protected peptides to give peptide-dye conjugates, e.g. 11.

Figure 2:
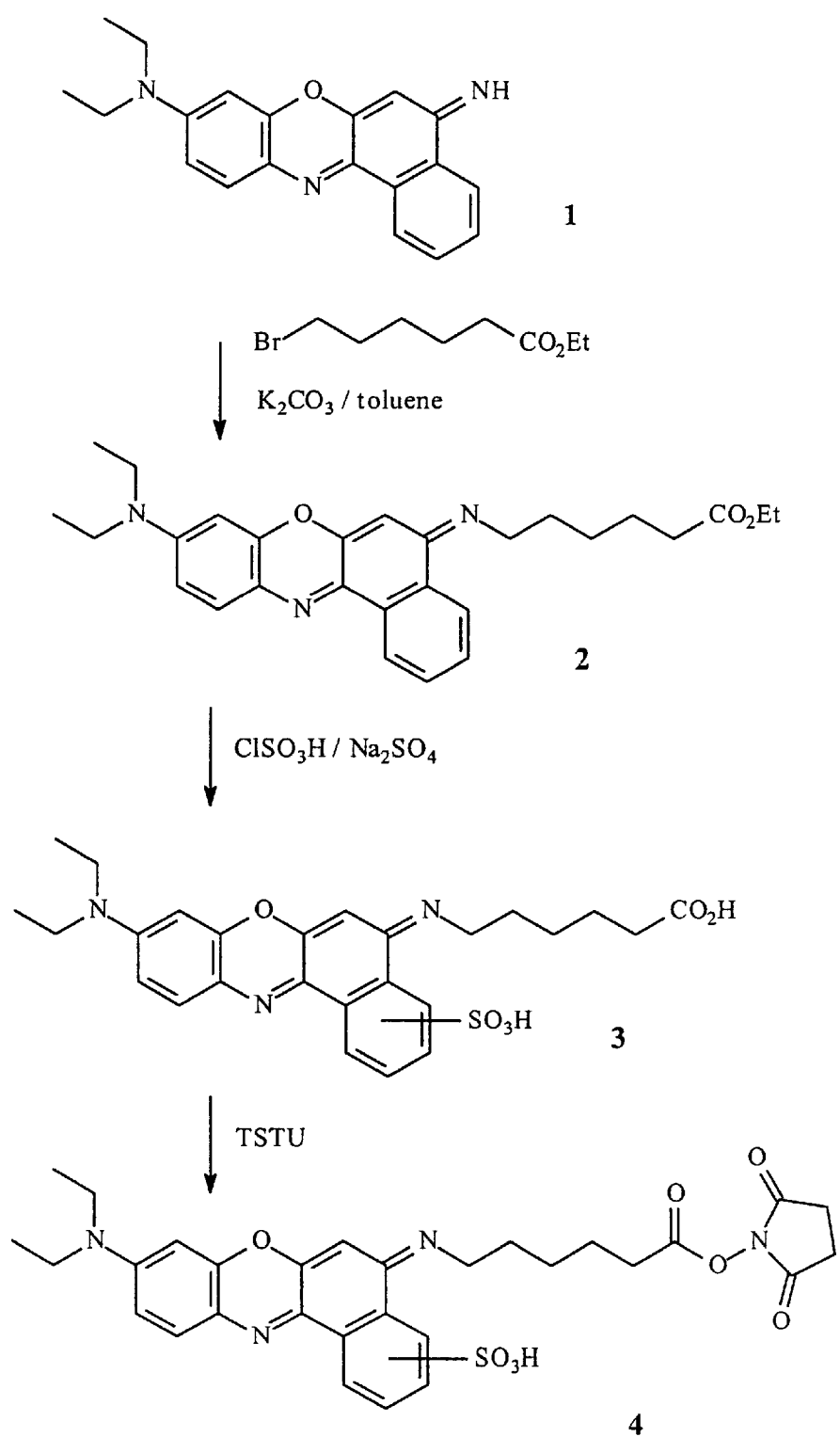
FIG. 2 shows a synthetic route to NHS ester 4, compounds 1 to 4.

During the course of sulfonation, esters of linking groups on the C3 and C7 amino substituents may be hydrolyzed, e.g. chlorosulfonation of 2 to give 3 (FIG. 2). The resulting carboxylic acid group is conveniently activated to form a reactive linking group to react with a substrate. FIG. 2 shows conversion of 3 to the corresponding active ester, N-hydroxysuccinimide with the coupling reagent, TSTU (O-(N-Succinimidyl)-N,N,N',N'-tetramethyluronium tetrafluoroborate (Example 4). Alternatively, the ester or carboxylic acid groups may be reduced to hydroxyl and phosphitylated to give highly reactive phosphoramidite compounds, III.

One group of preferred compounds according to structures I and II are those compounds in which C3 and C7 amino groups are substituted with aliphatic cationic chains. The aliphatic cationic chain typically comprises a total of 4 to 20 non-hydrogen atoms and has from 1 to 4 heteroatoms, e.g. nitrogen, which contribute positive charges under the conditions in which the dye is used. For example, $R^3$ or $R^7$ may be $-(CH_2)_n-NR_2$, $-(CH_2)_n-{}^+NR_3$, $-(CH_2)_n-{}^+NR_2-(CH_2)_n-{}^+NR_3$ and $-(CH_2)_n-{}^+NR_2-(CH_2)_n-{}^+NR_3$, where each n is 2 or 3, and each R is independently selected from the group consisting of hydrogen and $C_1-C_6$ alkyl. Not including the positive charge contributed by the C7 imminium nitrogen of the parent [8,9]benzophenoxazine ring, the cationic chain has at least one positive charge and typically not more than four positive charges under the conditions in which the dye is used. The positive charges are typically based upon amino or imino groups, although other elements which can support a positive charge, such as sulfur, phosphorous and iodine, may also be used to the extent that these cations are stable under the conditions of use.

Aryl ring substituents, $R^1$, $R^2$, $R^4$, $R^6$, $R^{11}$, $R^{12}$, $R^{13}$ and $R^{14}$, may bear reactive linking groups which couple with substrates or form energy transfer dye compounds. The reactive linking groups may be nucleophilic functionality, e.g. amino, thiol, or hydroxyl, or electrophilic functionality, e.g. active ester, disulfide, halide, or epoxide. For example, an aryl ring substituent may be aminomethyl, which may react as an amino nucleophile or be further converted to an electrophilic reactive linking group. Aminomethylation, chloromethylation, and hydroxymethylation of aryl rings are well known reactions in the art.

Following the synthetic methods above, a wide range of dye compounds may be prepared (FIGS. 8 and 9).

Those of skill in the art will appreciate that many of the compounds encompassed by structure I as well as the compound species specifically described above, may exhibit the phenomena of tautomerism, conformational isomerism, geometric isomerism and/or stereo isomerism. As the formulae drawings within this specification and claims can represent only one of the possible tautomeric, conformational isomeric, enantiomeric or geometric isomeric forms, it should be understood that the invention encompasses any tautomeric, conformational isomeric, enantiomeric and/or geometric isomeric forms of the compounds having one or more of the utilities described herein.

As a specific example, reference is made throughout the specification to C3 amino and C7 amino substituents. As this nomenclature corresponds to the illustrated structural formulae, which represent only one of several possible tautomeric forms (or resonance structures) of the compounds, it will be understood that these references are for convenience only, and that any such references are not intended to limit the scope of the compounds described herein.

In addition, those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

The compounds of the invention may bear multiple positive or negative charges. Typically, the net charge of the dyes of the invention will be negative. The counter ions associated with the dyes are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the dyes in association with any type of counter ion. Moreover, as the compounds can exists in a variety of different forms, the invention is intended to encompass not only forms of the dyes that are in association with counter ions (e.g., dry salts), but also forms that are not in association with counter ions (e.g., aqueous or organic solutions).

may be labelled with a donor dye at the carboxyl terminus and an acceptor dye at an internal cysteine or lysine sidechain (Komoriya, "Compositions for the detection of proteases in biological samples and methods of use thereof", U.S. Pat. No. 5,605,809). In the energy transfer dye of the invention, at least one of the donor or acceptor dyes which label a substrate is a sulfonated 3,7-diamino-[8,9] benzophenoxazine dye. Other dyes comprising the energy transfer dye may be any fluorescent moiety which undergoes the energy transfer process with a sulfonated [8,9] benzophenoxazine dye, including a fluorescein, rhodamine, and a cyanine dye.

Energy transfer dyes have advantages for use in the simultaneous detection of multiple labelled substrates in a mixture, such as DNA sequencing. A single donor dye can be used in a set of energy transfer dyes so that each dye has strong absorption at a common wavelength. By then varying the acceptor dye in the energy transfer set, the acceptor dyes can be spectrally resolved by their respective emission maxima. Energy transfer dyes also provide a larger effective Stokes shift than non-energy transfer dyes. The Stokes shift is the difference between the excitation maximum, the wavelength at which the donor dye maximally absorbs light, and the emission maximum, the wavelength at which the acceptor maximally emits light.

In a preferred embodiment, the linker between the donor dye and acceptor dye includes a functional group which gives the linker some degree of structural rigidity, such as an alkene, diene, an alkyne, a five and six membered ring having at least one unsaturated bond or a fused ring structure. The donor dye and the acceptor dye of the energy transfer dye may be attached by linkers which have the examplary structures:

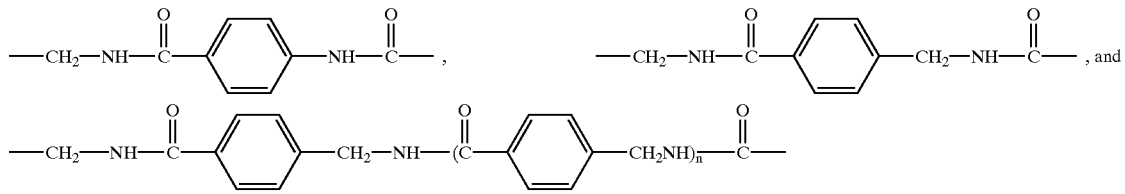

V.3 Energy Transfer Dye Compounds

In another aspect, the present invention comprises energy transfer dye compounds containing dye compounds such as those defined by structure I or II above. Generally, the energy transfer dyes of the present invention include a donor dye which absorbs light at a first wavelength and emits excitation energy in response, an acceptor dye which is capable of absorbing the excitation energy emitted by the donor dye and fluorescing at a second wavelength in response. The donor dye may be attached to the acceptor dye through a linker, the linker being effective to facilitate efficient energy transfer between the donor and acceptor dyes (Lee, "Energy transfer dyes with enhanced fluorescence", U.S. Pat. No. 5,800,996, issued Sep. 1, 1998; Lee "Energy transfer dyes with enhanced fluorescence", U.S. Pat. No. 5,945,526, issued Aug. 31, 1999; Mathies, "Fluorescent labels and their use in separations", U.S. Pat. No. 5,654,419, issued Aug. 5, 1997). Alternatively, the donor dye and the acceptor dye may be labelled at different attachment sites on the substrate. For example, an oligonucleotide may be labelled with a donor dye at the 5' terminus and an acceptor dye at the 3' terminus. A peptide wherein n is 1 or 2.

The attachment sites of the linker between the donor dye and acceptor dye of an energy transfer dye may be at any position where one or both of the donor dye and acceptor dye is a dye of the present invention. Preferred attachment sites include C3 and C7 amino.

The energy transfer dye compound is covalently attached to a substrate through a linker. The linker may be a bond, $C_1$–$C_{12}$ alkyldiyl or $C_6$–$C_{20}$ aryldiyl and bearing functional groups including amide, carbamate, urea, thiourea, phosphate, phosphorothioate, and the like. Preferred linkers include 1,2-ethyldiyl and 1,6-hexyldiyl. The attachment sites of the linker between the energy transfer dye and the substrate may be at any position on the energy transfer dye, where one or both of the donor dye and acceptor dye is a dye of the present invention. Where the substrate is a nucleoside or nucleotide, a preferred attachment site on the substrate is on the nucleobase. Where the substrate is an oligonucleotide, preferred attachment sites include the 3' and 5' terminii. Where the substrate is a peptide or protein, preferred attachment sites include the amino and carboxyl termini, and lysine residue amino substituents.

V.4 Labelling Reagents of the Dyes

The present invention comprises labelling reagents wherein sulfonated 3,7-diamino-[8,9]benzophenoxazine fluorescent dyes are in reactive form to react with substrates. In another aspect, the present invention comprises substrates labelled, i.e. conjugated with the dyes of the invention, formula I. Substrates can be virtually any molecule or substance to which the dyes of the invention can be conjugated, including by way of example and not limitation, proteins, polypeptides, polysaccharides, nucleosides, nucleotides, polynucleotides, lipids, solid supports, organic and inorganic polymers, and combinations and assemblages thereof, such as chromosomes, nuclei, living cells (e.g., bacteria or other microorganisms, mammalian cells, tissues, etc.), and the like. The dyes are conjugated with the substrate via an optional linker by a variety of means, including hydrophobic attraction, ionic attraction, and covalent attachment. Preferably, the dyes are conjugated to the substrate via covalent attachment.

Labelling typically results from mixing an appropriate reactive dye and a substrate to be conjugated in a suitable solvent in which both are soluble, using methods well-known in the art (Hermanson, Bioconjugate Techniques, (1996) Academic Press, San Diego, Calif. pp. 40–55, 643–71), followed by separation of the conjugate from any unconjugated starting materials or unwanted by-products. The dye conjugate can be stored dry or in solution for later use.

The dyes may include a reactive linking group at one of the substituent positions or covalent attachment of the dye to another molecule. Reactive linking groups are moieties capable of forming a covalent bond, typically electrophilic functional groups capable of reacting with nucleophilic molecules, such as alcohols, alkoxides, amines, hydroxylamines, and thiols. Examples of reactive linking groups include succinimidyl ester, isothiocyanate, sulfonyl chloride, sulfonate ester, silyl halide, 2,6-dichlorotriazinyl, pentafluorophenyl ester, phosphoramidite, maleimide, haloacetyl, epoxide, alkylhalide, allyl halide, aldehyde, ketone, acylazide, anhydride, and iodoacetamide.

Figure 4:
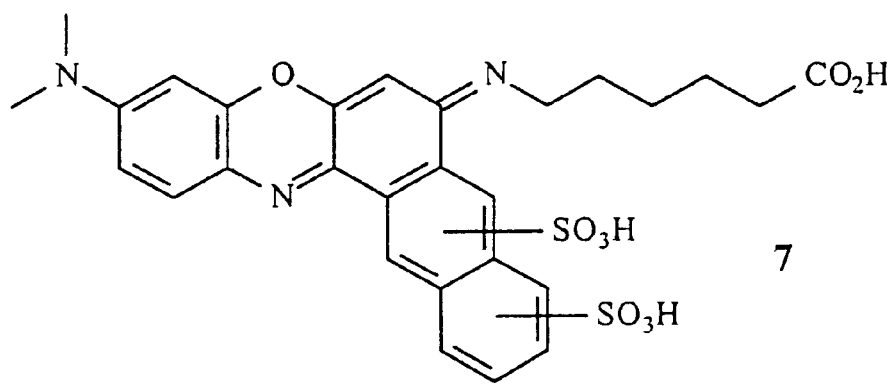
FIG. 4 shows a sulfonation reaction to form 7 and activation to form NHS ester 8.
Figure 4:
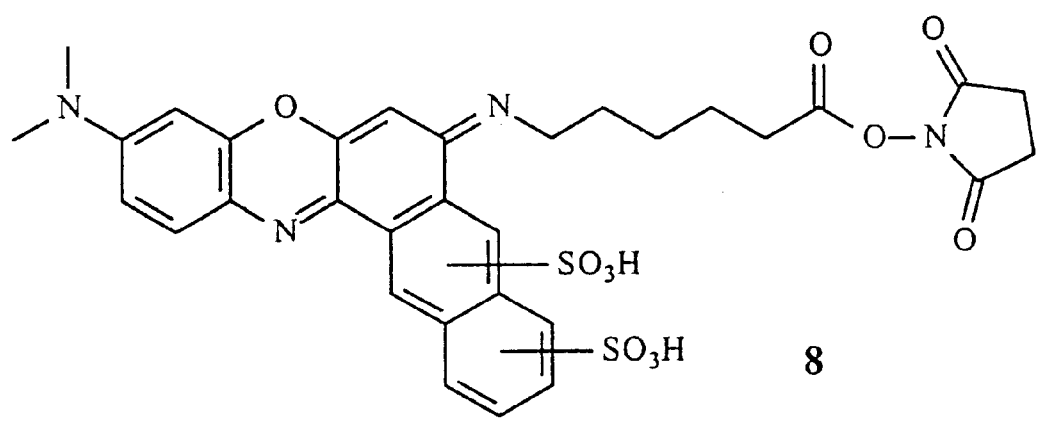

A preferred reactive linking group is N-hydroxysuccinimidyl ester (NHS) of a carboxyl group substituent of the sulfonated [8,9]benzophenoxazine dye (FIGS. 2, 4, 5). The NHS ester form of the dye is a preferred labelling reagent. The NHS ester of the dye may be preformed, isolated, purified, and/or characterized, or it may be formed in situ and reacted with a nucleophilic group of a substrate, such as an oligonucleotide, a nucleotide, a peptide, or the like. Typically, the carboxyl form of the dye is activated by reacting with some combination of a carbodiimide reagent, e.g. dicyclohexylcarbodiimide, diisopropylcarbodiimide, or a uronium reagent, e.g. TSTU (O-(N-Succinimidyl)-N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate), an activator, such as 1-hydroxybenzotriazole (HOBt), and N-hydroxysuccinimide to give the NHS ester of the dye. Preferred substituent positions for NHS esters on the sulfonated [8,9]benzophenoxazine dyes of the invention are $R^3$ and $R^7$. A representative example of an NHS ester are structures 4, 8, 13 in FIGS. 2, 4, 5 respectively.

In some cases, the dye and the substrate may be coupled by in situ activation of the dye and reaction with the substrate to form the dye-substrate conjugate in one step. For example, in Example 11, the C7 amino group of dye 10 is coupled directly with the carboxyl of the tetramer peptide with activator BOP (Benzotriazol-1-yloxy-tris(dimethylamino)phosphonium hexafluorophosphate) to give amide-linked, peptide-dye conjugate 11.

Other activating and coupling reagents include TBTU (2-(1H-benzotriazo-1-yl)-1-1,3,3-tetramethyluronium hexafluorophosphate), TFFH (N,N',N",N'"-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydro-quinoline), DCC (dicyclohexylcarbodiimide); DIPCDI (diisopropylcarbodiimide), MSNT (1-(mesitylene-2-sulfonyl)-3-nitro-1H-1,2,4-triazole, and aryl sulfonyl halides, e.g. triisopropylbenzenesulfonyl chloride.

Another preferred reactive linking group is a phosphoramidite form of the dyes of the present invention. Phosphoramidite dye reagents are particularly useful for the automated synthesis of oligonucleotides labelled with the dyes of the invention. Oligonucleotides are commonly synthesized on solid supports by the phosphoramidite method (Caruthers, M. and Beaucage, S. "Phosphoramidite compounds and processes", U.S. Pat. No. 4,415,732, issued Nov. 15, 1983; Caruthers, M. and Matteucci, M. "Process for preparing polynucleotides", U.S. Pat. No. 4,458,066, issued Jul. 3, 1984; Beaucage, S. and Iyer, R. (1992) "Advances in the synthesis of oligonucleotides by the phosphoramidite approach", Tetrahedron 48:2223–2311).

The phosphoramidite reagents can be nucleosidic or non-nucleosidic. Non-nucleosidic forms of phosphoramidite dye reagents have the general formula III:

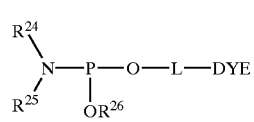

III where DYE is a protected or unprotected form of dye I, including energy transfer dye. L is a linker. $R^{24}$ and $R^{25}$ taken separately are $C_1$–$C_{12}$ alkyl, $C_4$–$C_{10}$ aryl, and cycloalkyl containing up to to carbon atoms, or $R^{24}$ and $R^{25}$ taken together with the phosphoramidite nitrogen atom form a saturated nitrogen heterocycle. $R^{26}$ is a phosphite ester protecting group which prevents unwanted extension of the oligonucleotide. Generally, $R^{26}$ is stable to oligonucleotide synthesis conditions yet is able to be removed from a synthetic oligonucleotide product with a reagent that does not adversely affect the integrity of the oligonucleotide or the dye. Preferably, $R^{26}$ is: (i) methyl, (ii) 2-cyanoethyl; —$CH_2CH_2CN$, or (iii) 2-(4-nitrophenyl)ethyl; —$CH_2CH_2$(p-$NO_2$Ph). Preferred embodiments of phosphoramidite reagents are where: (i) $R^{24}$ and $R^{25}$ are each isopropyl, (ii) $R^{24}$ and $R^{25}$ taken together is morpholino, (iii) L is $C_1$–$C_{12}$ alkyl, (iv) $R^{26}$ is 2-cyanoethyl, and (v) DYE is attached at $R^3$ or $R^7$ by a linker. Phosphoramidite dye reagents III effect labelling of a substrate with a single fluorescent dye of the invention. Where the substrate is an oligonucleotide, the dye will be attached at the 5' terminus of the oligonucleotide, as a consequence of the 3' to 5' direction of synthesis. Other phosphoramidite dye reagents, nucleosidic and non-nucleosidic allow for labelling at other sites of an oligonucleotide, e.g. 3' terminus, nucleobase, internucleotide linkage, sugar. Labelling at the nucleobase, internucleotide linkage, and sugar sites allows for internal and multiple labelling with fluorescent dyes.

The dyes may be converted to a non-nucleosidic, phosphoramidite dye labelling reagent, for example those shown in FIG. 7. Where the dye contains a carboxyl group, the carboxyl may be activated, e.g. to the NHS, and amidated with 6-amino, 1-hexanol. The resulting hydroxyl may be phosphitylated with bis(diisopropylamino) cyanoethylphosphite or chloro, diisopropylamino, cyanoethylphosphine to give the phosphoramidite dye-labelling reagent (Theisen (1992) "Fluorescent dye phosphoramidite labelling of oligonucleotides", in *Nucleic Acid Symposium Series* No. 27, Oxford University Press, Oxford, pp. 99–100). Alternatively, the carboxyl group of the dye may be reduced to the hydroxyl, to be phosphitylated. Two exemplary phosphoramidite-dye reagents are shown in FIG. 7.

The phosphoramidite dye reagent III reacts with a hydroxyl group, e.g. 5' terminal OH of an oligonucleotide bound to a solid support, under mild acid activation, to form an internucleotide phosphite group which is then oxidized to an internucleotide phosphate group. In some instances, the dye may contain functional groups, e.g. C3 and C7 amines as in structure I, that require protection either during the synthesis of the phosphoramidite reagent or during its subsequent use to label molecules such as oligonucleotides. The protecting group(s) used will depend upon the nature of the functional groups, and will be apparent to those having skill in the art (Greene, T. and Wuts, P. *Protective Groups in Organic Synthesis*, 2nd Ed., John Wiley & Sons, New York, 1991). Generally, the protecting groups used should be stable under the acidic conditions (e.g. trichloroacetic acid, dichloroacetic acid) commonly employed in oligonucleotide synthesis to remove 5'-hydroxyl protecting groups (e.g., dimethoxytrityl) and labile under the basic conditions (ammonium hydroxide, aqueous methylamine) used to deprotect and/or cleave synthetic oligonucleotides from solid supports.

The exocyclic amines of adenine and cytosine of the oligonucleotide can be protected with benzoyl (bz) and the exocyclic amine of guanine can be protected with dimethylformamide (dmo or isobutyryl (ibu) using conventional procedures. Preferably, the nucleobase is protected with groups that are readily removed under mild basic conditions. For example, oligonucleotides synthesized with $dA^{bz}$, $dC^{bz}$ $dG^{dmf}$ and T phosphoramidites (and their corresponding 3' nucleoside solid supports) can be cleaved and deprotected in 60 minutes in concentrated ammonium hydroxide at 65° C.

V.4A Peptide/Protein Labelling

Peptides, proteins, antibodies, and other biopolymers comprised of amino acids and amino acid analogs may be covalently labelled by conjugation with the sulfonated [8,9] benzophenoxazine dyes of the invention. Typically, the dye is in electrophilic form, e.g. NHS reactive linking group, which reacts with a nucleophilic group of the peptide, e.g. amino terminus, or amino side chain of an amino acid such as lysine. Alternatively, the dye may be in nucleophilic form, e.g. amino- or thiol-reactive linking group, which may react with an electrophilic group of the peptide, e.g. NHS of the carboxyl terminus or carboxyl side chain of an amino acid. Labelled peptides, proteins, and antibodies may retain their specific binding and recognition properties in interacting with cell surface and intracellular components. The dye provides a detection element for localizing, visualizing, and quantitating the binding or recognition event. Peptides can also be labelled with two moieties, a fluorescent reporter and quencher, which together undergo fluorescence resonance energy transfer (FRET). The fluorescent reporter may be partially or significantly quenched by the quencher moiety in an intact peptide. Upon cleavage of the peptide by a peptidase or protease, a detectable increase in fluorescence may be measured (Knight, C. (1995) "Fluorimetric Assays of Proteolytic Enzymes", Methods in Enzymology, Academic Press, 248:18–34).

A general protocol for conjugating the dyes in the NHS ester form to peptides entails dissolving the NHS esters in aqueous acetonitrile (the percentage of acetonitrile is determined by the hydrophobicity of the dye to attain solubility) with peptides in water (or aqueous acetonitrile solution if peptides were hydrophobic). Aqueous sodium bicarbonate buffer (1 M) is added to the solution to achieve 0.1 M buffer concentration while vortexing or shaking. The mixture is shaken at room temperature for 10 minutes to 30 minutes. The crude peptide-dye conjugate in the reaction mixture can be directly purified by reverse-phase HPLC Example 11 illustrates one such conjugate (FIG. 6).

V.4B Nucleotide Labelling

A preferred class of labelled substrates include conjugates of nucleosides and nucleotides that are labelled with the dyes of the invention. Such labelled nucleosides and nucleotides are particularly useful for labelling polynucleotides formed by enzymatic synthesis, e.g., labelled nucleotide 5'-triphosphates used in the context of PCR amplification, Sanger-type polynucleotide sequencing, and nick-translation reactions.

Nucleosides and nucleotides can be labelled at sites on the sugar or nucleobase moieties. Preferred nucleobase labelling sites include the 8-C of a purine nucleobase, the 7-C or 8-C of a 7-deazapurine nucleobase, and the 5-position of a pyrimidine nucleobase. Between a nucleoside or nucleotide and a dye, a linker may attach to a dye at any position.

The labelled nucleoside or nucleotide may be enzymatically incorporatable and enzymatically extendable. Nucleosides or nucleotides labelled with dyes of the invention may have formula (IV):

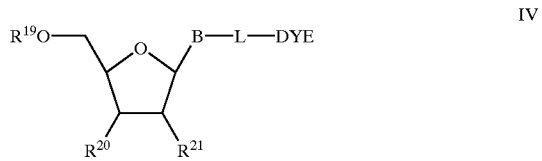

IV where DYE is a protected or unprotected form of dye I, including energy transfer dye. B is a nucleobase, e.g. uracil, thymine, cytosine, adenine, 7-deazaadenine, guanine, and 8-deazaguanosine. $R^{19}$ is H, monophosphate, diphosphate, triphosphate, thiophosphate, or phosphate ester analog. $R^{20}$ and $R^{21}$, when taken alone, are each independently H, HO, F and a phosphoramidite. Where $R^{20}$ or $R^{21}$ is phosphoramidite, $R^{19}$ is an acid-cleavable hydroxyl protecting group, e.g. dimethoxytrityl, which allows subsequent monomer coupling under automated synthesis conditions (Caruthers, "Phosphoramidite compounds and processes", U.S. Pat. No. 4,415,732, issued Nov. 15, 1983; Caruthers, "Process for preparing polynucleotides", U.S. Pat. No. 4,458,066, issued Jul. 3, 1984; Beaucage, S. and Iyer, R. (1992) "Advances in the synthesis of oligonucleotides by the phosphoramidite approach", Tetrahedron 48:2223–2311).

Where the labelled nucleoside or nucleotide is a terminator, $R^{20}$ and $R^{21}$ are selected to block polymerase-mediated template-directed polymerization. In terminator nucleotides, $R^{20}$ and $R^{21}$, when taken alone, are each independently H, F, and a moiety which blocks polymerase-mediated template-directed polymerization, or when taken together form 2'-3'-didehydroribose.

Linker L may be:

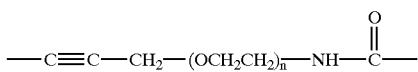

wherein n is 0, 1, or 2.

V.4C Oligonucleotide Labelling

Another preferred class of labelled substrates include conjugates of oligonucleotides and the dyes of the invention. Such conjugates may find utility as DNA sequencing primers, PCR primers, oligonucleotide hybridization probes, oligonucleotide ligation probes, double-labelled 5'-exonuclease (TaqMan™) probes, and the like (Fung "Amino-derivatized phosphite and phosphate linking agents, phosphoramidite precursors, and useful conjugates thereof", U.S. Pat. No. 4,757,141, issued Jul. 12, 1988; Andrus, 1995; Hermanson, Bioconjugate Techniques, (1996) Academic Press, San Diego, Calif. pp. 40–55, 643–71; Mullah (1998) "Efficient synthesis of double dye-labelled oligodeoxyribonucleotide probes and their application in a real time PCR assay", Nucl. Acids Res. 26:1026–1031). A labelled oligonucleotide may have formula (V):

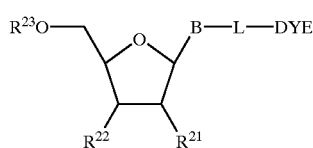

V where the oligonucleotide comprises 2 to 100 nucleotides. DYE is a fluorescent dye I, including energy transfer dye. B is a nucleobase, e.g. uracil, thymine, cytosine, adenine, 7-deazaadenine, guanine, and 8-deazaguanosine. L is a linker. $R^{21}$ is H, OH, halide, azide, amine, $C_1$–$C_6$ aminoalkyl, $C_1$–$C_6$ alkyl, allyl, $C_1$–$C_6$ alkoxy, $OCH_3$, or $OCH_2CH=CH_2$. $R^{22}$ is H, phosphate, internucleotide phosphodiester, or internucleotide analog. $R^{23}$ is H, phosphate, internucleotide phosphodiester, or internucleotide analog. In this embodiment, structure V, the nucleobase-labelled oligonucleotide may bear multiple dyes of the invention attached through the nucleobases. Nucleobase-labelled oligonucleotide V may be formed by: (i) enzymatic incorporation of enzymatically incorporatable nucleotide reagents IV where $R^{19}$ is triphosphate, by a DNA polymerase or ligase, and (ii) coupling of a nucleoside phosphoramidite reagent by automated synthesis. Whereas, nucleobase-labelled oligonucleotides V may be multiply labelled by incorporation of more than one incorporatable nucleotide IV, labelling with a dye label reagent such as III leads to singly 5'-labelled oligonucleotides,. according to formula VI:

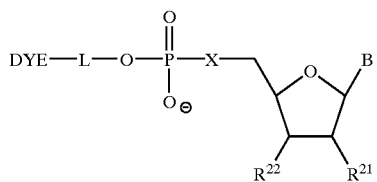

VI where X is O, NH, or S; $R^{21}$ is H, OH, halide, azide, amine, $C_1$–$C_6$ aminoalkyl, $C_1$–$C_6$ alkyl, allyl, $C_1$–$C_6$ alkoxy, $OCH_3$, or $OCH_2CH=CH_2$; $R^{22}$ is H, phosphate, internucleotide phosphodiester, or internucleotide analog; and $R^{23}$ is H, phosphate, internucleotide phosphodiester, or internucleotide analog. L is alkyl, aryl, or polyethyleneoxy. Preferably, L is n-hexyldiyl.

In a first method for labelling synthetic oligonucleotides, a nucleophilic functionality, e.g. a primary aliphatic amine, is introduced at a labelling attachment site on an oligonucleotide, e.g. a 5' terminus. After automated, solid-support synthesis is complete, the oligonucleotide is cleaved from the support and all protecting groups are removed. The nucleophile-oligonucleotide is reacted with an excess of a label reagent containing an electrophilic moiety, e.g. isothiocyanate or activated ester, e.g. N-hydroxysuccinimide (NHS), under homogeneous solution conditions (Hermanson, Bioconjugate Techniques, (1996) Academic Press, San Diego, Calif. pp. 40–55, 643–71; Andrus, A. "Chemical methods for 5' non-isotopic labelling of PCR probes and primers" (1995) in PCR 2: A Practical Approach, Oxford University Press, Oxford, pp. 39–54).

In a second, direct labelling, method, a label is directly incorporated into the oligonucleotide during or prior to synthesis (Mullah, "Solid support reagents for the direct synthesis of 3'-labelled polynucleotides", U.S. Pat. No. 5,736,626, issued Apr. 7, 1998; Nelson, "Multifunctional controlled pore glass reagent for solid phase oligonucleotide synthesis", U.S. Pat. No. 5,141,813, issued Aug. 25, 1992). The direct labelling method is preferred because it (i) does not require a post-synthesis reaction step, thereby simplifying the synthesis of labelled polynucleotides; and (ii) voids the problems associated with the low reaction yield (<60%) typically encountered with the two-step solution labelling method, namely: (a) purification of the labelled oligonucleotide from excess label; (b) purification of the labelled oligonucleotide from unlabelled oligonucleotide; (c) high costs due to the low product yield and laborious analytical and purification procedures, and; (d) irreversible capping of the nucleophilic functionality during synthesis. Certain fluorescent dyes and other labels have been functionalized as phosphoramidite reagents for 5' labelling (Theisen (1992) "Fluorescent dye phosphoramidite labelling of oligonucleotides", in Nucleic Acid Symposium Series No. 27, Oxford University Press, Oxford, pp. 99–100).

Labelled oligonucleotides VI may be formed by automated synthesis with phosphoramidite reagents III. Alternatively, labelled oligonucleotides VI may be formed by reacting a reactive linking group form , e.g. NHS, of a dye, e.g. 4, with a 5'-aminoalkyl oligonucleotide.

Generally, if the labelled oligonucleotide is made by enzymatic synthesis, the following procedure may be used. A target DNA is denatured and an oligonucleotide primer is annealed to the template DNA. A mixture of enzymatically-incorporatable nucleotides or nucleotide analogs capable of supporting continuous template-directed enzymatic extension of the primed target (e.g., a mixture including dGTP, dATP, dCTP and dTTP or dUTP) is added to the primed target. At least a fraction of the nucleotides is labelled with a dye I as labelled terminators, IV. A polymerase enzyme is next added to the mixture under conditions where the polymerase enzyme is active. A labelled oligonucleotide is formed by the incorporation of the labelled nucleotides or terminators during polymerase-mediated strand synthesis. In an alternative enzymatic synthesis method, two primers are used instead of one: one complementary to the (+) strand of the target and another complementary to the (−) strand of the target, the polymerase is a thermostable polymerase and the reaction temperature is cycled between a denaturation temperature and an extension temperature, thereby exponentially synthesizing a labelled complement to the target sequence by PCR (Innis (1990) *PCR Protocols*, Eds., Academic Press).

In one preferred post-synthesis chemical labelling method an oligonucleotide is labelled as follows. An NHS form of a dye according to structure I is dissolved or suspended in DMSO and added in excess (10–20×) to a 5'-aminohexyl oligonucleotide in 0.25 M bicarbonate/carbonate buffer at about pH 9 and allowed to react for 6 hours, e.g., U.S. Pat. No. 4,757,141. The dye labelled oligonucleotide VII can be separated from unreacted dye by passage through a size-exclusion chromatography column eluting with buffer, e.g., 0.1 molar triethylamine acetate (TEAA). The fraction containing the crude labelled oligonucleotide VII is further purified by reverse phase HPLC employing gradient elution.

V.5A Cell-Surface and Bead-Based Assay Methods

The sulfonated 3,7-diamino-[8,9]benzophenoxazine dyes and reagents of the invention are well suited for cell surface receptor assays. The dyes can also be used to label substrates, e.g. peptides, proteins, and polynucleotides, for subsequent detection of cell surface components in a broad range of contexts, including, e.g., in solution, on beads, surfaces, in whole-cell assays, in flow cytometry, in electrophoretic gel matrices, on blots and the like.

Direct quantification of cellular fluorescence intensity and enumeration of fluorescently labelled events, e.g. cell surface binding of peptide-dye conjugates may be conducted on an system (FMAT™ 8100 HTS System PE Biosystems, Foster City, Calif.) that automates mix-and-read, non-radioactive assays with live cells or beads (Miraglia, "Homogeneous cell- and bead-based assays for high throughput screening using fluorometric microvolume assay technology", (1999) J. of Biomolecular Screening 4:193–204). Dyes of the invention are detected in the red spectral region, minimizing high background fluorescence traditionally encountered using blue-green laser systems arising from plate cells or screening compounds. This technique is used to measure the binding of fluorescent-labelled substrates, such as peptides and proteins labelled with the dyes of the invention, to receptors present on, or inside, cells. Applications using the dyes of the invention also include cell surface receptor binding assays, inmmunocapture assays, fluorescence linked immunosorbent assays (FLISA), caspase-cleavage (Zheng, "Caspase-3 controls both cytoplasmic and nuclear events associated with Fas-mediated apoptosis in vivo", (1998) Proc. Natl. Acad. Sci. USA 95:618–23), apoptosis (Vermes, "A novel assay for apoptosis. Flow cytometric detection of phosphatidylserine expression on early apoptotic cells using fluorescein labelled Annexin V" (1995) J. Immunol. Methods 184:39–51) and cytotoxicity assays. Fluorometric microvolume assay technology can be used to identify the up or down regulation by a molecule that is targeted to the cell surface (Swartzman, "A homogeneous and multiplexed immunoassay for high-throughput screening using fluorometric microvolume assay technology", (1999) Anal. Biochem. 271:143–51).

The dyes of the invention may also be used in non-cell based assays, e.g. enzyme assays, drug screening assays to detect the binding of compounds to proteins or other targets, and assays of proteins, peptides or nucleic acids in clinical samples. For example, the dyes may be used to label capture proteins, e.g. streptavidin. The resulting dye-conjugate can bind with a biotinylated antibody which is bound to a substrate peptide or protein. In an immunocapture assay, a second antibody is immobilized or coated on a solid carrier, e.g. a bead or particle. When the second antibody also binds the substrate peptide or protein, fluorescence from the bead can be measured. Unbound fluorescence, from unbound dye-conjugate is ignored by the image analysis detection algorithm, obviating separation and washing steps.

V.5B Nucleic Acid Detection Methods

Non-isotopically labelled oligonucleotides are essential components in many important molecular biology applications, such as polymerase chain reaction (PCR) amplification, DNA sequencing, antisense transcriptional and translational control of gene expression, genetic analysis, and DNA probe-based diagnostic testing (Kricka, L. (1992) *Nonisotopic DNA Probe Techniques*, Academic Press, San Diego, pp.3–28). Fluorescence detection of fluorescent dye-labelled oligonucleotides is the basis for nucleic acid sequence detection assays such as 5' exonuclease assay (Livak, "Self-quenching fluorescence probe", U.S. Pat. No. 5,723,591, issued Mar. 3, 1998), FRET hybridization (Tyagi, S. and Kramer, F. (1996) "Molecular Beacons: Probes that fluoresce upon hybridization", Nature Biotechnology, 14:303–08), genetic linkage mapping (Dib (1996) "A comprehensive genetic map of the human genome based on 5,264 microsatellites", Nature 380:152–54) and oligonucleotide-ligation assay (Grossman (1994) "High-density multiplex detection of nucleic acid sequences: oligonucleotide ligation assay and sequence-coded separation", Nucl. Acids Res. 22:4527–34).

In a preferred category of methods referred to herein as "fragment analysis" or "genetic analysis" methods, polynucleotide fragments labelled with sulfonated 3,7-diamino-[8,9]benzophenoxazine dyes are generated through template-directed enzymatic synthesis using labelled primers or nucleotides, e.g. by ligation or polymerase-directed primer extension; the fragments are subjected to a size-dependent separation process, e.g., electrophoresis or chromatography; and, the separated fragments are detected subsequent to the separation, e.g., by laser-induced fluorescence (Hunkapiller, "Real time scanning electrophoresis apparatus for DNA sequencing", U.S. Pat. No. 4,811,218, issued Mar. 7, 1989). In a particularly preferred embodiment, multiple classes of polynucleotides are separated simultaneously and the different classes are distinguished by spectrally resolvable labels, including dyes of the invention.

Preferably, the chain termination methods of DNA sequencing, i.e. dideoxy DNA sequencing, or Sanger-type sequencing, and fragment analysis is employed (Sanger (1977) "DNA sequencing with chain-terminating inhibitors", Proc. Natl. Acad. Sci. USA 74:5463–5467). Exemplary chain-terminating nucleotide analogs include the 2',3'-dideoxynucleoside 5'-triphosphates (ddNTP) which lack the 3'-OH group necessary for 3' to 5' DNA chain elongation. Primers or ddNTP may be labelled with the dyes of the invention and detected by fluorescence after separation of the fragments by high-resolution electrophoresis. Dyes can be linked to functionality on the 5' terminus of the primer, e.g. amino (Fung, "Amino-derivatized phosphite and phosphate linking agents, phosphoramidite precursors, and useful conjugates thereof", U.S. Pat. No. 4,757,141, issued Jul. 12, 1988), on the nucleobase of a primer; or on the nucleobase of a dideoxynucleotide, e.g. via alkynylamino linking groups (Khan, "Substituted propargylethoxyamido nucleosides, oligonucleotides and methods for using same", U.S. Pat. No. 5,770,716, issued Jun. 23, 1998, and U.S. Pat. No. 5,821,356, issued Oct. 13, 1998; Hobbs, F. and Trainor, G. "Alkynylamino-nucleotides", U.S. Pat. No. 5,151,507, issued Sep. 29, 1992).

Each of the terminators bears a different fluorescent dye and collectively the terminators of the experiment bear a set of dyes including one or more from the dyes of the invention. In a preferred fragment analysis method, fragments labelled with dyes are identified by relative size, i.e. sequence length. Correspondence between fragment size and sequence is established by incorporation of the four possible terminating bases ("terminators") and the members of a set of spectrally resolvable dyes (Bergot, "Spectrally resolvable rhodamine dyes for nucleic acid sequence determination", U.S. Pat. No. 5,366,860, issued Nov. 22, 1994).

The covalent joining of nucleic acid probes by ligase enzymes is one of the most useful tools available to molecular biologists. When two probes are annealed to a template nucleic acid where the two probes are adjacent and without intervening gaps, a phosphodiester bond can be formed between a 5' terminus of one probe and the 3' terminus of the other probe by a ligase enzyme, (Whiteley, "Detection of specific sequences in nucleic acids", U.S. Pat. No. 4,883,750, issued 1989; Landegren, (1988) "A ligase mediated gene detection technique", Science 241:1077–80; Nickerson, "Automated DNA diagnostics using an ELISA-based oligonucleotide assay" (1990) Proc. Natl. Acad. Sci USA 87:8923–27). Oligonucleotide ligation assays detect the presence of specific sequences in target DNA sample. Where one or both probes are labelled with a dye, the ligation product may be detected by fluorescence.

Polynucleotides labelled with the dyes of the present invention may be additionally labelled with moieties that affect the rate of electrophoretic migration, i.e. mobility-modifying labels. Mobility-modifying labels include polyethyleneoxy units, —(CH$_2$CH$_2$O)$_n$— where n may be 1 to 100 (Grossman, U.S. Pat. No. 5,624,800, Issued Apr. 29, 1997). Preferably, n is from 2 to 20. The polyethyleneoxy units may be interspersed with phosphate groups. Specifically labelling sulfonated sulfonated 3,7-diamino-[8,9] benzophenoxazine dye-labelled polynucleotides with additional labels of polyethyleneoxy of discrete and known size allows for separation by electrophoresis, substantially independent of the number of nucleotides in the polynucleotide. That is, polynucleotides of the same length may be discriminated upon the bases of spectrally resolvable dye labels and mobility-modifying labels. Polynucleotides bearing both dye labels and mobility-modifying labels may be formed enzymatically by ligation or polymerase extension of the single-labelled polynucleotide or nucleotide constituents.

Subsequent to electrophoretic separation, the dye-polynucleotide conjugates are detected by measuring the fluorescence emission from the dye labelled polynucleotides. To perform such detection, the labelled polynucleotides are illuminated by standard means, e.g. high intensity mercury vapor lamps, lasers, or the like. Preferably the illumination means is a laser having an illumination beam at a wavelength above about 600 nm. More preferably, the dye-polynucleotides are illuminated by laser light generated by a He—Ne gas laser or a solid-state diode laser. The fluorescence is then detected by a light-sensitive detector, e.g., a photomultiplier tube, a charged coupled device, or the like. Exemplary electrophoresis detection systems are described elsewhere (Hoff, "Real-time scanning fluorescence electrophoresis apparatus for the analysis of polynucleotide fragments", U.S. Pat. No. 5,543,026, issued Aug. 6, 1996; Mathies, "Capillary array confocal fluorescence scanner and method", U.S. Pat. No. 5,274,240, issued Dec. 28, 1993; Hunkapiller, "Real time scanning electrophoresis apparatus for DNA sequencing", U.S. Pat. No. 4,811,218, issued Mar. 7, 1989).

VI.6 Kits

The invention includes kits comprising the sulfonated sulfonated 3,7-diamino-[8,9]benzophenoxazine dyes of the invention and/or their labelled conjugates. In one embodiment, the kits are useful for conjugating the dyes of the invention to other molecules, i.e. substrates. Such kits generally comprise a dye of the invention including an optional linking moiety and reagents, enzymes, buffers, solvents, etc. suitable for conjugating the dye to another molecule or substance.

In one embodiment, the kits are useful for labelling enzymatically synthesized oligonucleotides and polynucleotides with the dyes of the invention. Such kits generally comprise a labelled enzymatically-incorporatable nucleotide or nucleotide analog according to the invention, a mixture of enzymatically-incorporatable nucleotides or nucleotide analogs capable of supporting continuous primer extension and a polymerase enzyme. Preferably, the labelled enzymatically-incorporatable nucleotide or nucleotide analog is a compound according to structure IV, most preferably a labelled terminator. Preferred polymerases are thermostable, such as AMPLITAQ® DNA polymerase FA (PE Biosystems, Foster City, Calif.).

In another embodiment, the kits are useful for labelling synthetic oligonucleotides with the phosphoramidite dye reagents of the invention. Such kits generally comprise a phosphoramidite dye reagent, other synthesis reagents, and/or solid supports (Andrus, "Automated system for polynucleotide synthesis and purification" U.S. Pat. No. 5,262,530, issued Nov. 16, 1993) optionally for carrying out oligonucleotide synthesis.

In other kit embodiments, kits comprising peptides or proteins labelled with the dyes of the invention and antibody-coated beads are useful for bead-based immunocapture assays. Kits comprising peptides or proteins labelled with the dyes of the invention and reagents for binding the conjugate to a surface receptor of a cell are useful for cell surface receptor detection. V.7 EXAMPLES The invention having been described, the following Examples are offered by way of illustration, and not limitation.

Example 1

Synthesis of 1

Nile Blue Chloride (Aldrich, ~90%, 1.18 g, 3 mmol) was suspended in 100 ml water at 65° C. for 30 min. 100 ml of 0.5 M aqueous NaOH was added. The basic dye was extracted with methylene chloride three times (100 ml each). The organic layers were combined and dried with anhydrous Na$_2$SO$_4$. After evaporation, free base 1 was dried with an oil pump overnight (FIG. 2).

Example 2

Synthesis of 2

Free base 1 (200 mg, 0.63 mmol) was dissolved in 20 ml anhydrous toluene. Potassium carbonate, K$_2$CO$_3$ (Aldrich, 260 mg, 1.89 mmol) and ethyl 6-bromohexanoate (Aldrich, 336 µl, 1.89 mmol) were added. The mixture was refluxed under argon for 18 hours. After cooling, the mixture was purified with a flash silica gel column (90% CH$_2$Cl$_2$/10% CH$_3$OH as the eluent). 290 mg of Compd. B was obtained (yield 71%). M+1 calculated 460.3, found 460.5 (FIG. 2).

Example 3

Synthesis of 3

Compound 2 (HCl salt, 10 mg, 20 µmol) and anhydrous sodium sulfate (Aldrich, 300 mg) were added to methylene chloride (2 ml) and chlorosulfonic acid (Aldrich, 2 ml). The mixture was stirred at 70° C. for 4 hours. Then more chlorosulfonic acid (20 ml) and anhydrous sodium sulfate (600 mg) were added. The mixture was stirred at 70° C. for 18 more hours. After cooling, the reaction mixture was added to ice (around 100 g) dropwise. The solution was diluted with water (50-fold), and was loaded to a reverse-phased HPLC column directly.

Generally, reverse-phased HPLC was conducted under the following conditions: Flow rate: 4 ml/min. Mobile phases: Buffer A: 0.1% TFA in water; Buffer B: 0.085% TFA in acetonitrile. Gradient: Buffer B was linearly increased from 0% (100% Buffer A) to 70% (30% Buffer A) in 15 minutes; Buffer B was then linearly increased to 100% in 2 minutes. After running with Buffer B for 2 minutes, Buffer B was linearly decreased to 0% in 2 minutes. Detector: 630 nm (or 280 nm if compounds were not red-fluorescent dyes).

After evaporation and drying, 10 mg of Compd. C was obtained (yield 89.6%). M+1 calculated 512.2, found 512.3 (FIG. 2).

Example 4

Synthesis of 4

Compound 3 (Trifluoroacetic acid salt, 10 mg, 16 µmol) was dissolved in DMF (2 ml). O-(N-Succinimidyl)-N,N,N', N'-tetramethyluronium tetrafluoroborate (TSTU) (Fluka, 60 mg, 2001 µmol) and triethylamine (Aldrich, 2.0 µl, 14 µmol) were added. The mixture was stirred at room temperature for 30 minutes. The mixture was purified by reverse-phased HPLC. According to the HPLC result, all of 3 was converted to 4. Excitation maximum wavelength of Compd. 4 was 643 nm, and emission maximum wavelength was 680 nm. M+1 calculated 609.2, found 609.3 (FIG. 2).

Example 5

Synthesis of 5

Figure 3:
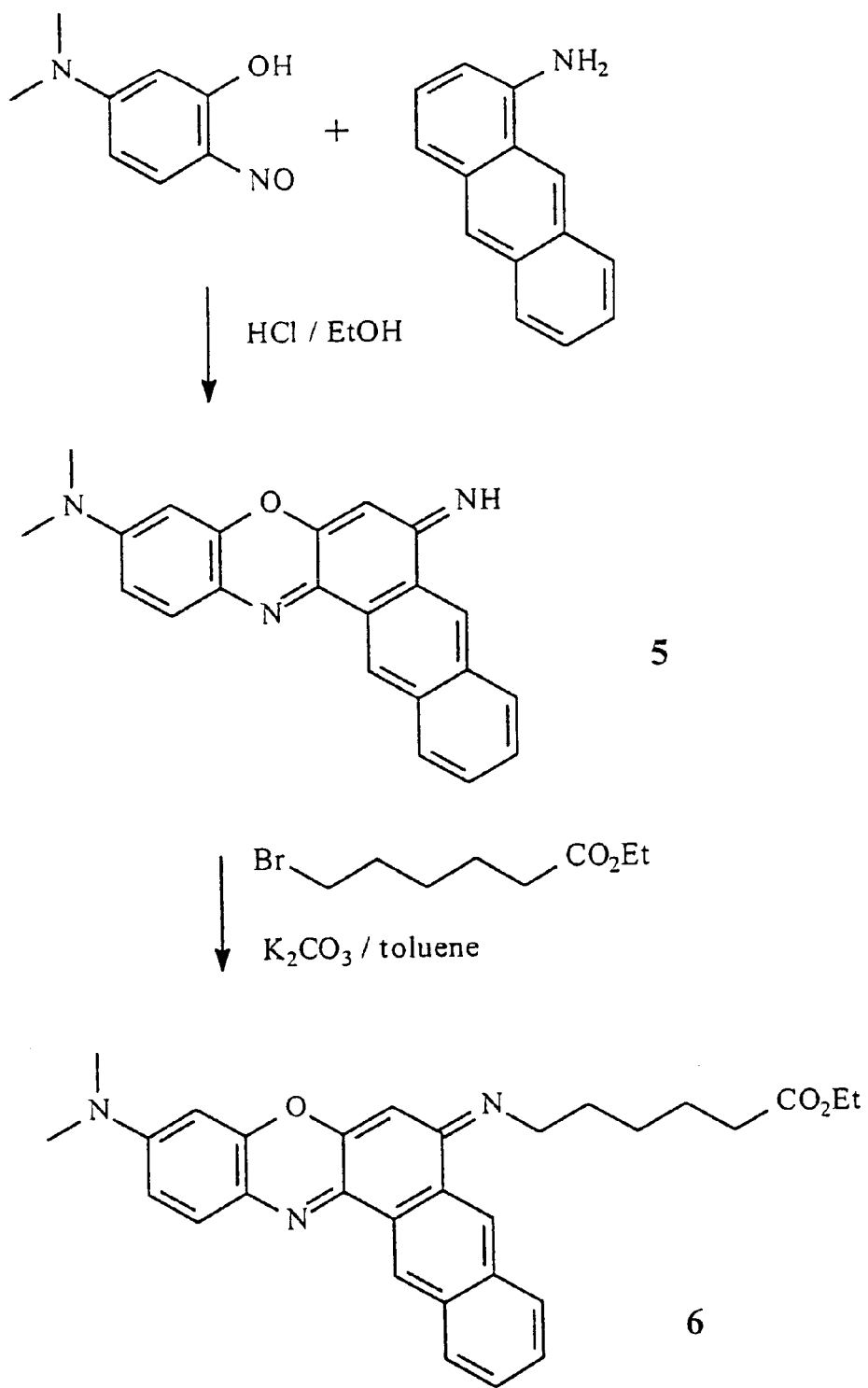
FIG. 3 shows a cyclization reaction to form 5 and alkylation to form intermediate 6.

2-Nitroso-5-dimethylaminophenol hydrochloride (TCI America, 203 mg, 1 mmol), 1-aminoanthracene (Aldrich, 193 mg, 1 mmol) and hydrochloric acid (Aldrich, 37 wt. %, 2 ml, 24 mmol) were dissolved in ethanol (100 ml). The mixture was refluxed for 18 hours. After cooling, the solvents were removed under pressure. The residue was purified with a flash silica gel column (10% methanol/90% methylene chloride/0.1% acetic acid as the eluent) to give 5. M+1 calculated 340.1, found 340.3 (FIG. 3).

Example 6

Synthesis of 6

Compd. 5 (acetic acid salt, 30 mg, 75 µmol) in methanol (2 ml) was added to 30 ml of 0.5 mM aqueous sodium hydroxide solution. The basic form of 5 was obtained with chloroform extraction, evaporation and drying. Potassium carbonate (Aldrich, 138 mg, 1 mmol), ethyl 6-bromohexanoate (Aldrich, 178 µl, 1 mmol) and dry toluene (50 ml) were added to the basic dye. The mixture was refluxed for 18 hours. After cooling, volatile reagents were removed under pressure. The residue was purified with a flash silica gel column (10% methanol/90% methylene chloride/0.1% acetic acid as the eluent) to give 6. M+1 calculated 482.2, found 482.3 (FIG. 3).

Example 7

Synthesis of 7

Compound 6 (acetic acid salt, 10 mg, 18 µmol), anhydrous sodium sulfate (500 mg) were added to chlorosulfonic acid (Aldrich, 4 ml). The mixture was stirred at 70° C. for 14 hours. After cooling, the mixture was added dropwise to wet ice (150 g). The solution was then stirred at 60° C. for 3 hours. After dilution with water (50-fold), the solution was loaded onto a reverse-phased HPLC column directly and pure 7 was obtained. Excitation maximum wavelength of 7 is 650 nm, and emission maximum wavelength is 698 nm. M+1 calculated 614.1, found 614.3 (FIG. 4).

Example 8

Synthesis of 8

Compound 7 (TFA salt, 1 mg, 1.4 µmol) was dissolved in DMF (2 ml). TSTU (60 mg, 200 µmol) and sodium bicarbonate (Aldrich, 8.0 mg) were added. The mixture was purged with argon constantly for 2 hours. The reaction mixture was purified with reverse-phased HPLC to give 8. M−1 calculated 709.1, found 709.3 (FIG. 4).

Example 9

Synthesis of 9

8-Amino-2-naphthalenesulfonic acid (Aldrich, 1.115 g, 5 mmol), ethyl 6-bromohexanoate (1.067 ml, 6 mmol) and 1,8-bis(dimethylamino)naphthalene ("protonsponge" Aldrich, 2.14 g, 10 mmol) were dissolved in anhydrous acetonitrile (150 ml). The mixture was refluxed under argon for 18 hours. The solvent was evaporated and the residue was purified with reverse-phased HPLC to give 9. MS of Compd. I, M−1calculated 364.1, found 364.0 (FIG. 5).

Example 10

Synthesis of 10

3-(3-hydroxy-4-nitroso-N-propylanilino)propane-sulfonic acid (Fluka, 302 mg, 1 mmol) and 8-amino-2-naphthalenesulfonic acid (Aldrich, 223 mg, 1 mmol) were dissolved in ethanol (200 ml) and hydrochloric acid (37 wt. %, 4 ml). The mixture was refluxed for 18 hours. After evaporating the solvent, the residue was purified with reverse-phased HPLC to give 10 (FIG. 6).

Example 11

Synthesis of 11

DEVD peptide: Acetyl-Asp(But)Glu(But)ValAsp(But)-COOH was prepared on chlorotrityl polystyrene resin by typical solid-phase peptide synthesis methods with a Model 433 Peptide Synthesizer (PE Biosystems, Foster City, Calif.) and Fmoc/HBTU chemistry (Fields, G. and Noble, R. (1990) "Solid phase peptide synthesis utilizing 9-fluoroenylmethoxycarbonyl amino acids", Int. J. Peptide Protein Res. 35:161–214). The crude protected peptide on resin was cleaved with 1% TFA in methylene chloride for 10 minutes. The pH of the filtrate was immediately raised to 8 with 4-dimethylaminopyridine. After evaporating the volatile reagents, the crude protected peptide (Acetyl-Asp(But) Glu(But)ValAsp(But)-COOH) was obtained and used directly to conjugate sulfonated [8,9]benzophenoxazine dyes.

The crude protected peptide DEVD: Acetyl-Asp(But)Glu (But)ValAsp(But)-COOH (SEQ. ID NO. 1), Benzotniazol-1-yloxy-tris(dimethyl-amino)phosphonium hexafluorophosphate (BOP) (Advanced ChemTech, 22 mg, 50 µmol) and dye 10 (TFA salt, 1 mg, 1.6 µmol) were dissolved in DMF (200 µl). The mixture was shaken at room temperature for 72 hours. The solvent was completely removed, and the residual was deprotected with 30% TFA in methylene chloride for 30 minutes. After evaporation, the mixture was purified by reverse-phased HPLC to give 11. Mass spectroscopy: M+1 calculated 1006.5, found 1006.3 (FIG. 6).

Example 12

Synthesis of 12

Compound 9 (4.3 mg, 12 μmol) and 3-(3-hydroxy-4-nitroso-N-propylanilino)propane-sulfonic acid (Fluka, 7.2 mg, 24 μmol) were dissolved in ethanol (50 ml) and hydrochloric acid (37 wt. %, 4 ml). The mixture was refluxed for 18 hours. The reaction mixture was purified with reverse-phased HPLC to give 12. Mass spectroscopy: M+1 calculated 620.2, found 620.3 (FIG. 5).

Example 13

Synthesis of 13

Compound 12 (1 mg, 1.6 μmol), TSTU (100 mg, 0.33 mmol) and triethylamine (2.23 μl, 16 μmol) were dissolved in DMF (5 ml). The mixture was purged with argon constantly for 1 hour. The mixture was purified with reverse-phased HPLC to give 13. Mass spectroscopy: M+1 calculated 717.2, found 717.3 (FIG. 5).

Example 14

Figure 11B:
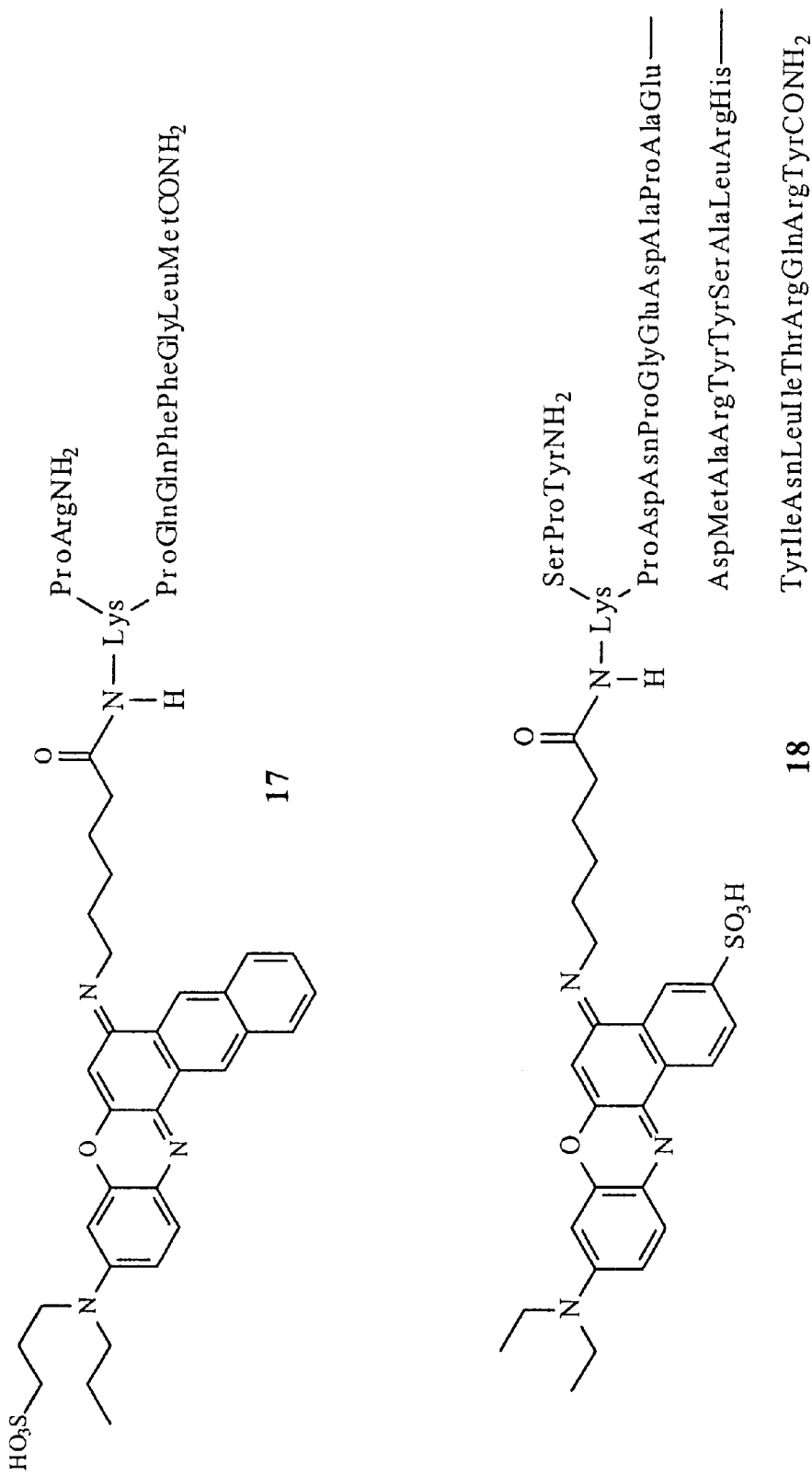

Synthesis of Dye Conjugates 14, 15, 16, 17 of Substance P Peptide Substance P Peptide H$_2$N-Arg-Pro-Lys$^3$-Pro-Gln-Gln-Phe-Phe-Gly-Leu-Met-CONH$_2$ (SEQ. ID NO. 2) was prepared by the method of EXAMPLE 11. The NHS form of sulfonated [8,9] benzophenoxazine dyes were prepared, e.g. 4, 8, 13, and coupled to the sidechain amino group of lysine$^3$ of Substance P peptide in aqueous acetonitrile containing NaHCO$_3$ with shaking at room temperature for 10 minutes to an hour. Conjugated dye-peptides (FIGS. 11A and 11B) were purified by reverse-phase HPLC.

Example 15

Synthesis of Dye Conjugate 18 from 4 and Neuropeptide Y Neuropeptide Y

H$_2$N-Tyr-Pro-Ser-Lys$^4$-Pro-Asp-Asn-Pro-Gly-Glu-Asp-Ala-Pro-Ala-Glu-Asp-Met-Ala-Arg-Tyr-Tyr-Ser-Ala-Leu-Arg-His-Tyr-Ile-Asn-Leu-Ile-Thr-Arg-Gln-Arg-Tyr-CONH$_2$ (SEQ. ID NO. 3) was prepared by the method of EXAMPLE 11. The NHS form of sulfonated [8,9] benzophenoxazine dye 4 was coupled to the sidechain amino group of lysine$^4$ of Neuropeptide Y in aqueous acetonitrile containing NaHCO$_3$ with shaking at room temperature for 10 minutes. Conjugated dye-peptide 18 (FIG. 11B) was purified by reverse-phase HPLC.

All publications, patents and patent applications mentioned in this specification are herein incorporated by reference to the same extent as if each individual publication, patent or patent application was specifically and individually indicated to be incorporated by reference.

The invention now having been fully described, it will be apparent to one of ordinary skill in the art that many changes and modifications can be made thereto without departing from the spirit or scope of the invention.

We claim:

1. A labelling reagent comprising a sulfonated 3,7-diamino-[8,9]benzophenoxazine dye and a reactive linking group defined by the formula:

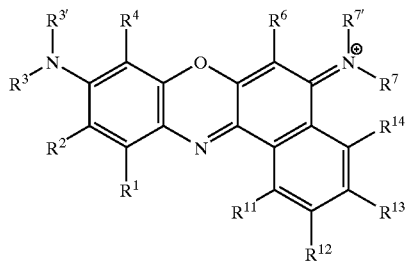

including any associated counter ions, wherein:

$R^1$, $R^2$, $R^4$, $R^6$, $R^{11}$, $R^{12}$, $R^{13}$ and $R^{14}$, when taken alone, are separately hydrogen, sulfonate, carboxylate, phosphonate, phosphate, halogen, $C_1$–$C_6$ alkyl, $C_1$–$C_6$ aminoalkyl, $C_5$–$C_{14}$ aryl, $C_5$–$C_{14}$ aryl substituted with one or more of the same or different W groups, —OR$^A$, —SR$^A$, —NR$^A$R$^B$, —CN, —NO$_2$, —C(O)R$^A$ or a reactive linking group;

$R^1$ when taken together with $R^2$ is $C_5$–$C_{14}$ aryleno or $C_5$–$C_{14}$ aryleno substituted with one or more of the same or different W groups;

$R^3$, $R^{3'}$, $R^7$ and $R^{7'}$, when taken alone, are separately hydrogen, a reactive linking group, an aliphatic cationic chain, $C_1$–$C_6$ alkyl or $C_5$–$C_{14}$ aryl;

$R^3$ when taken together with $R^{3'}$ is $C_2$–$C_8$ alkyldiyl;

$R^7$ when taken together with $R^{7'}$ is $C_2$–$C_8$ alkyldiyl;

$R^{11}$ and $R^{12}$, when taken together, are $C_5$–$C_{14}$ aryleno or $C_5$–$C_{14}$ aryleno substituted with one or more of the same or different W groups;

$R^{12}$ and $R^{13}$, when taken together, are $C_5$–$C_{14}$ aryleno or $C_5$–$C_{14}$ aryleno substituted with one or more of the same or different W groups;

$R^{13}$ and $R^{14}$, when taken together, are $C_5$–$C_{14}$ aryleno or $C_5$–$C_{14}$ aryleno substituted with one or more of the same or different W groups;

each W is independently hydrogen, sulfonate, carboxylate, phosphonate, phosphate, halogen, $C_1$–$C_6$ alkyl, —OR$^A$, —SR$^A$, —NR$^A$R$^B$, —CN, —NO$_2$ or —C(O)R$^A$; and each R$^A$ and each R$^B$ is independently hydrogen or $C_1$–$C_6$ alkyl;

with the proviso that at least one of $R^1$, $R^2$, $R^4$, $R^6$, $R^{11}$, $R^{12}$, $R^{13}$ and $R^{14}$ is sulfonate, or $R^{12}$ and $R^{13}$ taken together are benzo containing at least one sulfonate attached to the benzo ring, or at least one of $R^3$, $R^{3'}$, $R^7$ and $R^{7'}$ is $C_1$–$C_6$ alkylsulfonate or $C_4$–$C_{10}$ arylsulfonate; and with the proviso that at least one of $R^3$, $R^{3'}$, $R^7$, $R^{7'}$, $R^{11}$, $R^{12}$, $R^{13}$ and $R^{14}$ is a reactive linking group.

2. The labelling reagent of claim 1 defined by the formula:

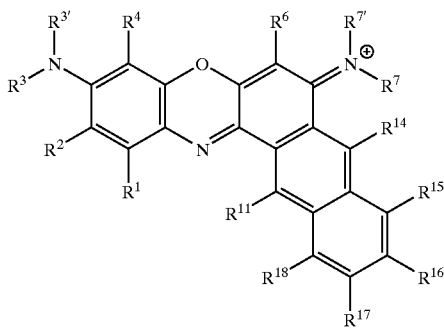

wherein $R^{15}$, $R^{16}$, $R^{17}$, and $R^{18}$ are separately hydrogen, sulfonate, carboxylate, phosphonate, phosphate, halogen, $C_1$–$C_6$ alkyl, $C_5$–$C_{14}$ aryl, $C_5$–$C_{14}$ aryl substituted with one or more of the same or different W groups, —$OR^A$, —$SR^A$, $NR^AR^B$, —CN, —$NO_2$, —$C(O)R^A$ or a reactive linking group.

3. The labelling reagent of claim 1 wherein
   $R^2$ and $R^3$ taken together with the C2-ring atom, C3 ring atom, and 3-nitrogen atom, form a 5- to 7-member ring whose ring atoms are selected from the group consisting of carbon, nitrogen, oxygen, and sulfur; or
   $R^{3'}$ and $R^4$ taken together with the 3-nitrogen atom, C3-ring atom, and C4-ring atom, form a 5- to 7-member ring whose ring atoms are selected from the group consisting of carbon, nitrogen, oxygen, and sulfur; or
   $R^6$ and $R^{7'}$ taken together with the C6-ring atom, C7-ring atom, and 7-nitrogen atom, form a 5- to 7-member ring whose ring atoms are selected from the group consisting of carbon, nitrogen, oxygen, and sulfur; or
   $R^7$ and $R^{14}$ taken together with the 7-nitrogen atom, C7-ring atom, C8-ring atom, and C14-ring atom, form a 5- to 7-member ring whose ring atoms are selected from the group consisting of carbon, nitrogen, oxygen, and sulfur.

4. The labelling reagent of claim 3 wherein the 5- to 7-member ring includes a gem-disubstituted carbon atom.

5. The labelling reagent of claim 4 wherein the gem disubstituted carbon atom is substituted with two $C_1$–$C_6$ alkyl groups which may be the same or different.

6. The labelling reagent of claim 5 wherein the $C_1$–$C_6$ alkyl groups are methyl.

7. The labelling reagent of claim 1 wherein $R^1$, $R^2$, $R^4$ and $R^6$ are each hydrogen.

8. The labelling reagent of claim 1 wherein $R^3$ and $R^{3'}$ are each independently $C_1$–$C_3$ alkyl.

9. The labelling reagent of claim 1 wherein $R^1$ and $R^2$ together are [1,2]benzeno, [1,2]naphthaleno or [2,3]naphthaleno.

10. The labelling reagent of claim 1 wherein $R^{11}$, $R^{12}$, $R^{13}$ and $R^{14}$ are each hydrogen.

11. The labelling reagent of claim 1 wherein $R^{11}$ and $R^{12}$ together are [1,2]benzeno.

12. The labelling reagent of claim 1 wherein $R^{12}$ and $R^{13}$ together are [1,2]benzeno.

13. The labelling reagent of claim 1 wherein $R^{13}$ and $R^{14}$ together are [1,2]benzeno.

14. The labelling reagent of claim 1 wherein the aliphatic cationic chain is —$(CH_2)_n$—$NR_2$, —$(CH_2)_n$—$^+NR_3$, —$(CH_2)_n$—$^+$—$NR_2$—$(CH_2)_n$—$NR_2$ or —$(CH_2)_n$—$^+NR_2$—$(CH_2)_n$—$^+NR_3$, each n is independently an integer from 2 to 3, and each occurrence of R is independently selected from hydrogen and $C_1$–$C_6$ alkyl.

15. The labelling reagent of claim 1 wherein alkylsulfonate is —$(CH_2)_n$—$SO_3H$, and n is an integer from 1 to 6.

16. The labelling reagent of claim 1 wherein arylsulfonate is:

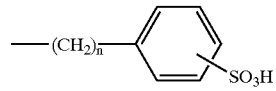

and n is 0 or 1.

17. The labelling reagent of claim 1 defined by one of the following formulas:

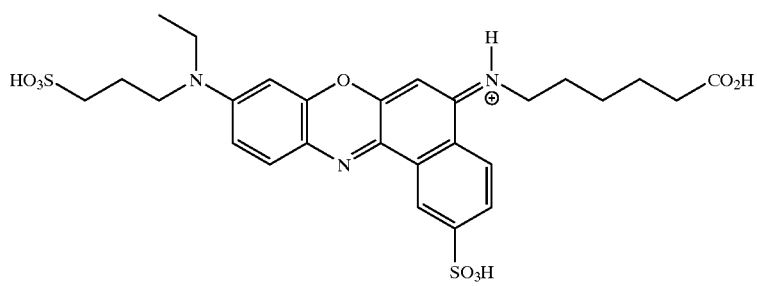

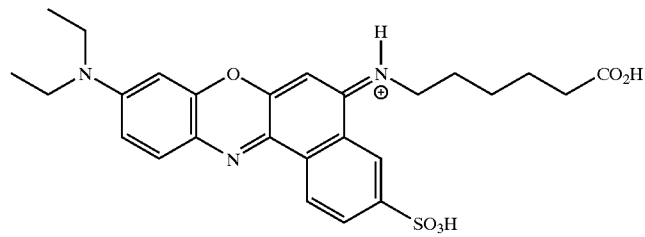

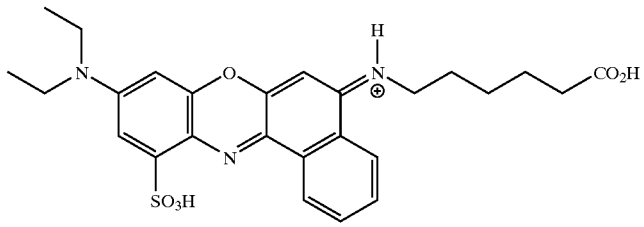

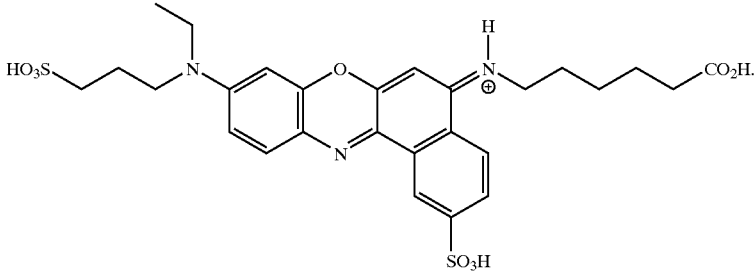

18. The labelling reagent of claim 1 defined by the formula:

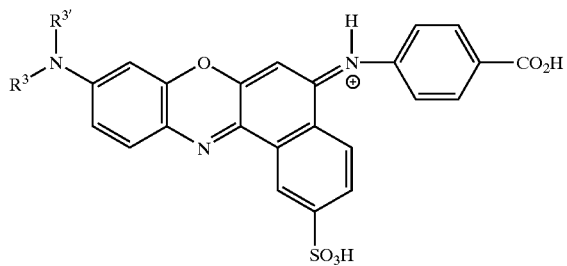

wherein $R^3$ and $R^{3'}$ are independently hydrogen or $C_1$–$C_6$ alkyl.

19. The labelling reagent of claim 1 defined by the formula:

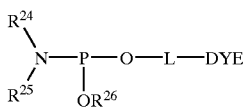

DYE is the sulfonated 3,7-diamino-[8,9] benzophenoxazine dye;
L is a linker;
$R^{24}$ and $R^{25}$ taken separately are $C_1$–$C_{12}$ alkyl, $C_4$–$C_{10}$ aryl, or cycloalkyl containing up to 10 carbon atoms; or $R^{24}$ and $R^{25}$ taken together with the phosphoramidite nitrogen atom form a saturated nitrogen heterocycle; and
$R^{26}$ is a phosphite ester protecting group.

20. The labelling reagent of claim 19 wherein $R^{26}$ is methyl, 2-cyanoethyl, or 2-(4-nitrophenyl)ethyl.

21. The labelling reagent of claim 19 wherein $R^{24}$ and $R^{25}$ are each isopropyl.

22. The labelling reagent of claim 19 wherein L is $C_1$–$C_{12}$ alkyldiyl.

23. The labelling reagent of claim 19 wherein L is attached to the 3-nitrogen atom or the 7-nitrogen atom of the sulfonated 3,7-diamino-[8,9]benzophenoxazine structure.

24. The labelling reagent of claim 19 defined by the formula:

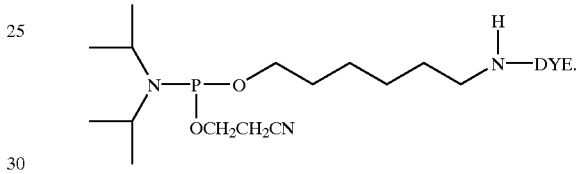

25. The labelling reagent of claim 1 wherein the reactive linking group is selected from amino, thiol, hydroxyl, carboxylic acid, N-hydroxysuccinimidyl ester, disulfide, a halide, an isothiocyanate, sulfonyl chloride, a silyl halide, 2,6-dichlorotriazinyl, pentafluorophenyl ester, a phosphoramidite, maleimide, haloacetyl, epoxide, an alkylhalide, an allyl halide, aldehyde, ketone, acylazide, anhydride, and iodoacetamide.

26. A compound comprising a substrate covalently attached by a bond or a linker to a sulfonated 3,7-diamino-[8,9]benzophenoxazine dye wherein the substrate is selected from a polynucleotide, a nucleotide, a nucleoside, a polypeptide, a carbohydrate, a ligand, a particle, and a surface; and the sulfonated 3,7-diamino-[8,9] benzophenoxazine dye is defined by the formula:

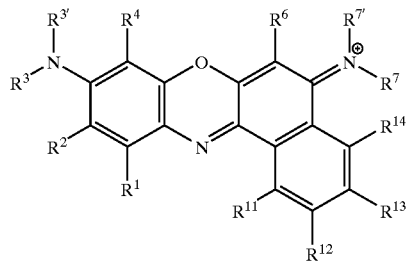

including any associated counter ions, wherein:
$R^1$, $R^2$, $R^4$, $R^6$, $R^{11}$, $R^{12}$, $R^{13}$ and $R^{14}$, when taken alone, are separately hydrogen, sulfonate, carboxylate, phosphonate, phosphate, halogen, $C_1$–$C_6$ alkyl, $C_1$–$C_6$ aminoalkyl, $C_5$–$C_{14}$ aryl, $C_5$–$C_{14}$ aryl substituted with one or more of the same or different W groups, —$OR^A$, —$SR^A$, —$NR^AR^B$, —CN, —$NO_2$, —$C(O)R^A$ or a linker;

$R^1$ when taken together with $R^2$ is $C_5$–$C_{14}$ aryleno or $C_5$–$C_{14}$ aryleno substituted with one or more of the same or different W groups;

$R^3$, $R^{3'}$, $R^7$ and $R^{7'}$, when taken alone, are separately hydrogen, a linker, an aliphatic cationic chain, $C_1$–$C_6$ alkyl or $C_5$–$C_{14}$ aryl;

$R^3$ when taken together with $R^{3'}$ is $C_2$–$C_8$ alkyldiyl;

$R^7$ when taken together with $R^{7'}$ is $C_2$–$C_8$ alkyldiyl;

$R^{11}$ and $R^{12}$, when taken together, are $C_5$–$C_{14}$ aryleno or $C_5$–$C_{14}$ aryleno substituted with one or more of the same or different W groups;

$R^{12}$ and $R^{13}$, when taken together, are $C_5$–$C_{14}$ aryleno or $C_5$–$C_{14}$ aryleno substituted with one or more of the same or different W groups;

$R^{13}$ and $R^{14}$, when taken together, are $C_5$–$C_{14}$ aryleno or $C_5$–$C_{14}$ aryleno substituted with one or more of the same or different W groups;

each W is independently hydrogen, sulfonate, carboxylate, phosphonate, phosphate, halogen, $C_1$–$C_6$ alkyl, —$OR^A$, —$SR^A$, $NR^AR^B$, —CN, —$NO_2$ or —$C(O)R^A$; and each $R^A$ and each $R^B$ is independently hydrogen or $C_1$–$C_6$ alkyl;

with the proviso that at least one of $R^1$, $R^2$, $R^4$, $R^6$, $R^{11}$, $R^{12}$, $R^{13}$ and $R^{14}$ is sulfonate, or $R^{12}$ and $R^{13}$ taken together are benzo containing at least one sulfonate attached to the benzo ring, or at least one of $R^3$, $R^{3'}$, $R^7$ and $R^{7'}$ is $C_1$–$C_6$ alkylsulfonate or $C_4$–$C_{10}$ arylsulfonate.

27. The compound of claim 26 wherein the substrate is defined by the formula:

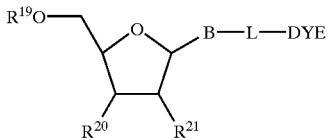

wherein DYE is the sulfonated 3,7-diamino-[8,9] benzophenoxazine dye;

L is a linker;

B is a nucleobase;

$R^{19}$ is H, monophosphate, diphosphate, triphosphate, or phosphate analog thereof; and $R^{20}$ and $R^{21}$, when taken alone, are each independently H, HO, F, a phosphoramidite group, or a moiety which blocks polymerase-mediated polymerization, or when taken together, form 2'-3'-didehydroribose.

28. The compound of claim 27 wherein B is uracil, thymine, cytosine, adenine, 7-deazaadenine, guanine, 7-deazaguanosine, 7-deaza-8-azaguanine, or 7-deaza-8-azaadenine.

29. The compound of claim 27 wherein L is:

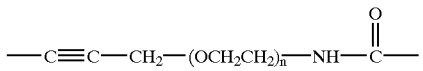

and n is 0, 1, or 2.

30. The compound of claim 27 which is enzymatically incorporatable.

31. The compound of claim 27 which is a terminator.

32. The compound of claim 31 wherein $R^{19}$ is triphosphate, α-thiotriphosphate, or triphosphate ester analog; and $R^{20}$ and $R^{21}$, when taken alone, are each independently H, F, or a moiety which blocks polymerase-mediated polymerization, or when taken together, form 2'-3'-didehydroribose.

33. The compound of claim 27 which is enzymatically extendable.

34. The compound of claim 26 wherein the substrate is defined by the formula:

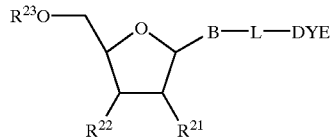

wherein the polynucleotide comprises two or more nucleotides;

DYE is the sulfonated 3,7-diamino-[8,9] benzophenoxazine dye;

L is a linker;

B is a nucleobase;

$R^{21}$ is H, OH, halide, azide, amine, $C_1$–$C_6$ aminoalkyl, $C_1$–$C_6$ alkyl, allyl, $C_1$–$C_6$ alkoxy, —$OCH_3$, or —$OCH_2CH=CH_2$; and $R^{22}$ and $R^{23}$ are independently H, phosphate, internucleotide phosphodiester, or internucleotide analog.

35. The compound of claim 26 wherein the substrate is defined by the formula:

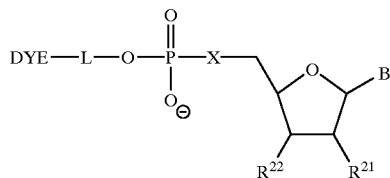

wherein the compound comprises two or more nucleotides;

DYE is the sulfonated 3,7-diamino-[8,9] benzophenoxazine dye;

L is a linker;

X is O, NH, or S;

B is a nucleobase;

$R^{21}$ is H, OH, halide, azide, amine, $C_1$–$C_6$ aminoalkyl, $C_1$–$C_6$ alkyl, allyl, $C_1$–$C_6$ alkoxy, —$OCH_3$, or —$OCH_2CH=CH_2$; and $R^{22}$ is internucleotide phosphodiester or internucleotide analog.

36. The compound of claim 35 wherein L is $C_1$–$C_{12}$ alkyldiyl.

37. The compound of claim 35 wherein L comprises —$(CH_2CH_2O)_n$—, and n is 1 to 100.

38. The compound of claim 26 defined by the formula: P—L—DYE, wherein P is a polypeptide; L is a linker; and DYE is the sulfonated 3,7-diamino-[8,9]benzophenoxazine dye.

39. The compound of claim 38 wherein L is an amide bond.

40. The compound of claim 38 wherein L is attached to P through a carboxyl terminus, an amino terminus, a lysine sidechain, an aspartic acid sidechain, or a glutamic acid sidechain.

41. The compound of claim 38 wherein P is streptavidin, a caspase-cleavage substrate, or an antibody.

* * * * *